(12) United States Patent
Birdwell et al.

(10) Patent No.: US 9,235,733 B2
(45) Date of Patent: Jan. 12, 2016

(54) MOBILE BIOMETRICS INFORMATION COLLECTION AND IDENTIFICATION

(76) Inventors: J. Douglas Birdwell, Oak Ridge, TN (US); N. Quentin Haas, Burlington, MA (US); Scott F. Hansen, Knoxville, TN (US)

( * ) Notice: Subject to any disclaimer, the term of this patent is extended or adjusted under 35 U.S.C. 154(b) by 753 days.

(21) Appl. No.: 13/403,505

(22) Filed: Feb. 23, 2012

(65) Prior Publication Data

US 2012/0148115 A1    Jun. 14, 2012

Related U.S. Application Data

(60) Continuation-in-part of application No. 13/209,278, filed on Aug. 12, 2011, now Pat. No. 8,412,463, which is a division of application No. 11/467,834, filed on Aug. 28, 2006, now Pat. No. 8,271,201, application No. 13/403,505, which is a continuation-in-part of application No. 12/684,539, filed on Jan. 8, 2010, now Pat. No. 8,301,392.

(60) Provisional application No. 61/448,467, filed on Mar. 2, 2011, provisional application No. 60/836,941, filed on Aug. 11, 2006, provisional application No. 61/193,927, filed on Jan. 9, 2009.

(51) Int. Cl.
| | |
|---|---|
| *G01N 33/50* | (2006.01) |
| *G06K 5/00* | (2006.01) |
| *G06K 9/00* | (2006.01) |
| *G06F 19/18* | (2011.01) |

(52) U.S. Cl.
CPC .. *G06K 5/00* (2013.01); *G06K 9/00* (2013.01); *G06F 19/18* (2013.01)

(58) Field of Classification Search
None
See application file for complete search history.

(56) References Cited

U.S. PATENT DOCUMENTS

| | | |
|---|---|---|
| 5,291,560 A | 3/1994 | Daugman |
| 7,594,612 B2 | 9/2009 | Bonalle et al. |
| 7,853,054 B2 | 12/2010 | Biswas et al. |
| 7,881,503 B2 | 2/2011 | Mason |
| 7,881,507 B2 | 2/2011 | Fyke |
| 8,719,584 B2 | 5/2014 | Mullin |
| 2011/0206243 A1 | 8/2011 | Vlcan |
| 2011/0288874 A1* | 11/2011 | Hinkamp ................. 705/1.1 |

OTHER PUBLICATIONS

Business Wire, "Market Watch: Popular Science Magazine Names MORIS(TM) one of the Best Innovations of 2010," Nov. 23, 2010, BI(2) Technologies, Plymouth, MA, one page.

* cited by examiner

*Primary Examiner* — Jason Sims
(74) *Attorney, Agent, or Firm* — Cameron LLP

(57) ABSTRACT

A biometric mobile device is capable of interacting with existing cellular, wireless, and wired telecommunication and other communication networks to support intelligence gathering, human body identification, special operations and other applications. A method of collecting biometric data at an accident or crime scene may comprise, for example, utilizing a camera to photograph the accident scene, collecting key entered data that may not be otherwise obtainable, using a fingerprint scanner to collect, digitize and store fingerprint data, using a lab-on-a-chip DNA profile device for collecting and analyzing a DNA specimen and generating identification and DNA profile data for bar code entry and other means for collecting any known form of biometric data including, but not limited to, vascular facial structure, dental structure, cornea, iris or other data which may be unique or limiting for identification purposes.

20 Claims, 33 Drawing Sheets

MOBILE BIOMETRICS INFORMATION COLLECTION AND IDENTIFICATION

This application is a continuation-in-part of U.S. application Ser. No. 13/209,278, filed Aug. 12, 2011, (now U.S. Pat. No. 8,412,463 issued Apr. 2, 2013), which is a division of U.S. application Ser. No. 11/467,834 filed Aug. 28, 2006, (now U.S. Pat. No. 8,271,201 issued Sep. 18, 2012), which claims the benefit of priority to U.S. Provisional Application Ser. No. 60/836,941, filed Aug. 11, 2006, is also a continuation-in-part of U.S. application Ser. No. 12/684,539, filed Jan. 8, 2010, which claims the benefit of priority to U.S. Provisional Application Ser. No. 61/193,927, filed Jan. 9, 2009 and claims the benefit of priority to U.S. provisional application Ser. No. 61/448,467, filed Mar. 2, 2011, of the same inventors. all patent applications being incorporated by reference as to their entire contents.

BACKGROUND

1. Technical Field

The field of the preferred embodiments is directed to a biometrics mobile telephone device and forensics software application for such a mobile device, and, in particular, to the collection of biometrics information for a human (or animal) body or remains including fingerprint, DNA, iris scan, voice for recognition or identification, vascular representation, dental structures, radio frequency identification tag, marks, scars and tattoos, and personal profile data via the mobile device and local or remote server or cloud software for making a probable identification of the collected biometric information to stored biometric information so that, for example, police, fire and rescue personnel may make an identification at an accident, terrorist event, battlefield, or crime scene.

2. Related Arts

Fingerprint and DNA profile storage for millions of humans in the United States are known from state, local and federal government as well as private sources, for example, the fingerprint and DNA profile data stored by the U.S. Department of Justice, Federal Bureau of Investigation. Biometric data are collected by Interpol and other international and domestic agencies as well for those who may be suspected, convicted and/or imprisoned for terrorist or criminal activity. Fingerprints are often voluntarily collected by state agencies at a child's birth for purposes of possible future use in the event of a kidnapping, victim identification or other reason for which parents voluntarily permit the collection and storage of their children's fingerprints and other biometric data in databases. Automatic fingerprint identification services (AFIS) are known whereby a set of prints may be automatically collected, digitally stored and compared for identification purposes at local police departments.

Analysis of an iris as a unique indicator of an individual is described in U.S. Pat. No. 5,291,560 entitled Biometric Personal Identification System Based on Iris Analysis. U.S. Pat. No. 7,594,612 assigned to American Express provides for retinal scan recognition in the design of a commercial transaction terminal. U.S. Pat. No. 7,853,054 provides a system for generating templates of a fingerprint input image similar to what may be used in AFIS. The system includes identification and verification steps, which compare the template generated with templates stored in a fingerprint database. U.S. Pat. No. 7,881,503 provides for validating the identity of a person using corneal imaging techniques. U.S. Pat. No. 7,881,507 assigned to Research in Motion Limited suggests that the known intelligent telephone known as the Blackberry® telephone may be soon equipped with a fingerprint scanner. A small number of mobile phones feature a dedicated fingerprint scanner, namely the Fujitsu F-01A mobile phone and the recently introduced Motorola Atrix mobile telephones. AuthenTec, a large supplier of fingerprint scanners for laptop computers, offers a line of fingerprint sensors targeted at Android phones. However, these are typically used for owner/user identification purposes to prevent unauthorized access to the device and are similar to the sliding fingerprint scanners on laptops which makes standard fingerprinting tedious. Fingerprint scanning may be easily added to intelligent telephones or iPad's by an auxiliary port or internally, for example, via camera or fingerprint scanner input. Already, it is known that many mobile devices automatically collect GPS data for current location, and such information can be utilized to identify an owner or user of a mobile device, or the information can be correlated with other information in a local or remote computer database to analyze the activities of one or more individuals. Also, most mobile telephones provide cameras for capturing images including close-up fingerprint images and bar codes. Auxiliary focusing devices can be utilized in order to focus sufficiently closely. For example, the simplest device is a convex or positive diopter lens. Indeed, it is known that one and two dimensional bar codes can be collected by such a camera, and these bar codes may represent, for example, personal identification data and DNA profile data respectively. The same cameras may capture crime and accident scenes, cornea and iris data, dental structure and forensic data of all sorts including fingerprint identification and iris photographic data. Fingerprints on standard fingerprint identification cards, as commonly utilized by law enforcement agencies, government bodies, and military organizations, may also be utilized, and the fingerprints on the cards may be digitized using such a camera. The camera may be digital or analog and, if the latter, be provided with a high resolution analog to digital converter.

It would be desirable for police, fire and rescue organizations to be provided with a biometric mobile device capable of collecting biometric data for a given human or animal body, an individual, and, either locally or with remote assistance such as by querying a remote computer database, identify or validate the identity of the individual. This biometric mobile device could also be used to test for narcotic or alcohol use or to identify suspect chemical or biological substances in the field by obtaining measurements from the substances and querying a local or remote computer database. All patents and published patent applications referred to above and herein should be deemed to be incorporated by reference as to their entire contents.

SUMMARY OF THE PREFERRED EMBODIMENTS

A biometric mobile device is capable of interacting with existing cellular, wireless (such as WiFi) and wired telecommunication and other communication networks to support intelligence gathering, human body identification, special operations and other applications. A satellite telephone may be utilized in a similar manner. Such a device may be associated with a server or cloud service and may comprise a software application and modifications as necessary to existing mobile phone device hardware to provide for a collection of a plurality of different biometric and related data. Herein is described a hardware and software solution that will quickly fulfill the need for biometric data collection, comparison and, for example, human identification using many off-the-shelf components, while keeping costs of hardware modifications and associated software requirements to a minimum. Such a biometric mobile device equipped with a biometric data collection and identification software application may utilize an external server and/or cloud application and database services as available to identify an individual with a given probability.

A method of collecting biometric data at an accident or crime scene may comprise, for example, utilizing a camera to photograph the accident scene, collecting key entered data that may not be otherwise obtainable, using a fingerprint scanner to collect, digitize and store fingerprint data, using a lab-on-a-chip or other portable DINA profile device for collecting and analyzing a DNA specimen and generating identification and DNA profile data for bar code entry and other means for collecting any known form of biometric data including, but not limited to, vascular facial structure, cornea, iris or other data which may be unique or limiting for identification purposes. As an alternative to the use of a barcode, a wireless or wired connection such as BlueTooth, Ethernet, or a USB port/connector may be utilized to transfer information between the DNA profile device or other device for acquisition or collection of forensic information and the biometric mobile device. A comparison may be made of all collected data for an unknown and compared with remote or local databases for known biometric data and a match be made ranking the likelihood that the match is indeed the individual hypothetically established in relation to a family pedigree, as described in published U.S. Patent Application 2008/0040046 of Feb. 4, 2008, (now U.S. Pat. No. 8,271,201 issued Sep. 18, 2012).

The base device selected for discussion herein will be the Motorola Atrix® telephone, a recently released smart telephone that is a GSM compatible with an integrated fingerprint scanner and runs on the Android platform. While this mobile device is selected as one alternative, as suggested above, a RIM Blackberry® telephone may be soon available with a fingerprint scanner. Already more and more smart phones are being equipped with cameras, GPS coordinate collection data and with bar code scanners and displays for viewing bar codes of one and two dimensions. Due to the ubiquitous nature of the Android operating system, MoBIC can be utilized on all mobile devices capable of running Android. Data collection requiring dedicated hardware (not including external data collection devices) would naturally be limited to devices with that hardware (e.g. integrated fingerprint scanners). Bioinformatics data collection may require interfacing with external data collection devices. Several USB fingerprint scanners exist, such as the UPEK Eikon TCRD4 USB Fingerprint reader. External USB iris scanners exist, such as the Hoyos Eyelock USB Iris Scanner for computer security purposes. These external could be incorporated by MoBIC to provide in-the-field acquisition of Iris bioinformatics data.

Once actuated, one embodiment of a biometric mobile device may comprises a touch display screen for showing a plurality of potential applications such as collection of DNA profile data, Mobile Disaster Victim Identification or Mobile DVI or Mobile Biometric Information Collection or MoBIC. Once selected, for example, MoBIC provides an introductory screen whereby a Browse, Search, new data, Import, Export, Sync (synchronize), Preferences (settings) or Exit and other selections may be made to enter MoBIC's utilities. If Browse is selected, then an ordering or database selection may be made. If new data, then, a predetermined number per display of profiles may be selected for entry along with applicable metadata such as date, time and location. If Search, one may search by a search term such as a key word or by name, age, height, weight, race, skin color, or other biometric. The search results may be posted to the device touchscreen (or other display) and scrolled using touch or a joystick (for example, via the Blackberry® phone central tab). An exemplary profile may comprise, but not be limited to comprise a name, age, weight, height, gender, facial, photographs, fingerprints, iris or cornea, left or right, scars, marks and tattoos (SMT) data, DNA profile data, dental data and the like. Methods of collection including fingerprint capture using dust or Super-Glue® glue, known chemical reagents and the like or iris or cornea data capture using a camera and such a close-up/distance camera will not be discussed in detail and are assumed known in the art. Generally, once collected from an accident or crime scene, an individual may be associated with a family pedigree, another family member by relation, or otherwise identified by use of local or remote service software for matching biometric data with known data to establish a match. Relationships to one or more other family members, or among a set of family members, may be described as a family pedigree using methods well-known in the art. A probability or other measure such as a measure of similarity may be calculated based on all collected data that there indeed is a match of biometric data for an individual to that of a known person or a member of a family pedigree.

The collected biometric data may be physically returned or transmitted to a central location where software may be run, for example, to resolve a DNA mixture per U.S. Pat. No. 7,162,372 or 7,672,789, (In particular, the University of Tennessee offers mixture deconvolution to police and fire and rescue organizations.) Peak fitting algorithms analyze two dimensional graphic data representing DNA profile peaks and perform allele peak fitting and attribute extraction, for example, per US Published Application No. 2009/022845 of Sep. 10, 2008, (now U.S. Pat. No. 8,645,073 issued Feb. 4, 2013). An automated expert system (STRESP) also exists for performing automated expert analysis, for example, per U.S. Pat. No. 7,640,223: 7,624,087; 7,665,719 or 7,840,519. U.S. Published Patent Application Nos. 2008/0040046 of Feb. 4, 2008, (now U.S. Pat. No. 8,271,201 issued Sep. 18, 2012), and 2010/0138374 of Jun. 3, 2010, (now U.S. Pat. No. 8,301, 392 issued Oct. 30, 2012) describe associating an unknown biological specimen with a family pedigree. This published application also describes an automated decision support tool for selecting family members of a family pedigree when, for example, one or more parents are unavailable for typing.

These and other features of embodiments of a biometric mobile device and method of identification will be discussed in connection with the drawings, a brief description of which follows.

BRIEF DESCRIPTION OF THE DRAWINGS

FIG. 7A provides a further selectable menu of options if an "order by" 520 of FIG. 5 is selected, for example, for a particular database whereby one or more search terms for a Boolean search are input via a keyboard, not shown, of an exemplary mobile telephone device of FIG. 1 and one may search, for example, by name, age and the like.

FIG. 8A provides an exemplary profile display screen showing target or unknown data associated with an individual including, for example, name, weight, height, facial, fingerprint, iris (cornea), scars, marks and tattoos (SMT), DNA specimen profile data and the like.

FIG. 9 illustrates a block diagram of a hardware environment that may be used according to an illustrative embodiment of the invention including a biometric intelligent mobile telephone featuring a data collection and identification software application, a communications interface, a bus, a server and the like.

DETAILED DESCRIPTION

Figure 1A:
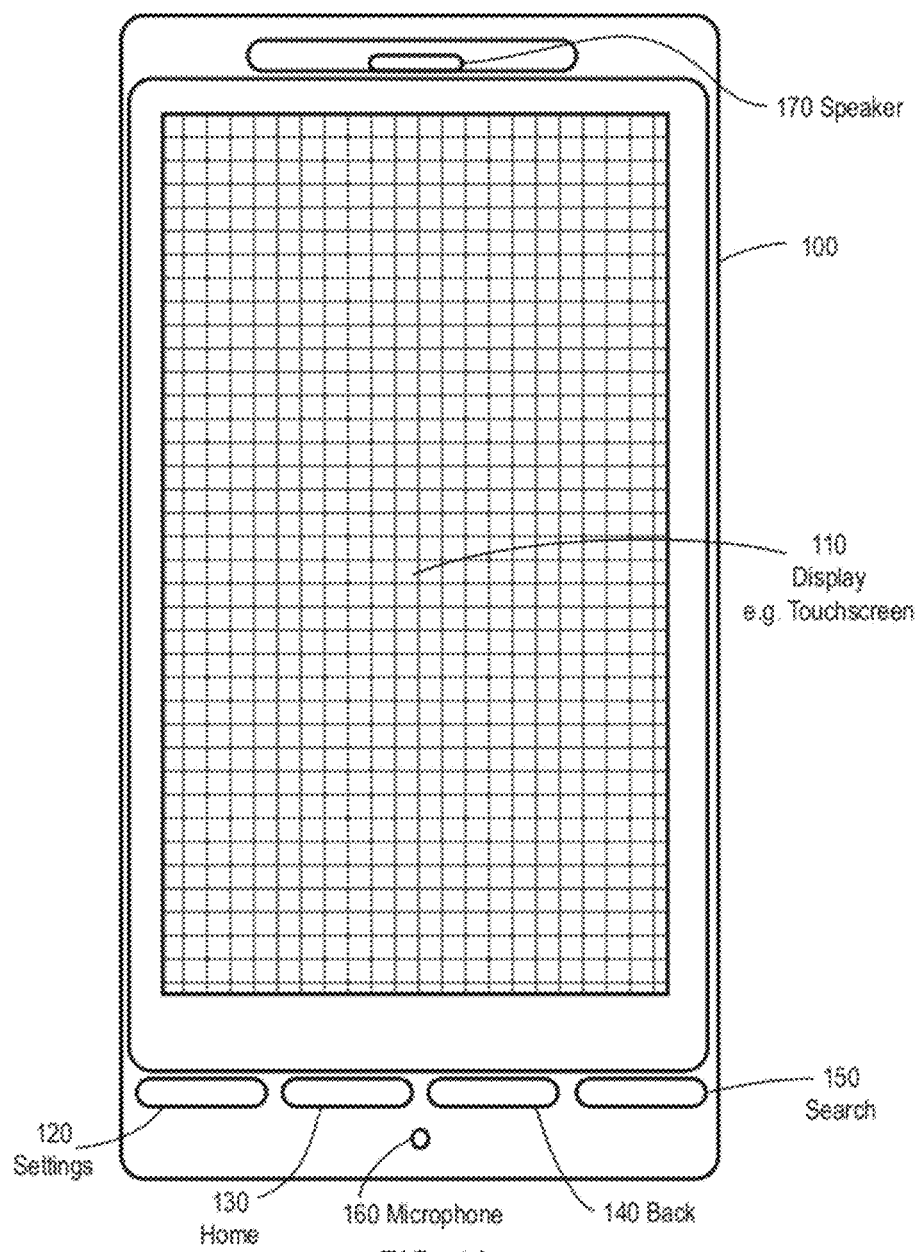
FIG. 1A provides a front side example of a typical intelligent mobile telephone (smart phone) or other larger device such as an iPad® computer manufactured by Apple Computer or any of numerous types of tablet personal computer running, for example, the Android 2.2 operating system, utilities and user interface from Google and the Open Handset Alliance. The device 100 includes a display which may be a touch screen capable of collecting fingerprint data, bar code data and the like, by way of example, a Motorola Atrix mobile telephone.
Figure 1B:
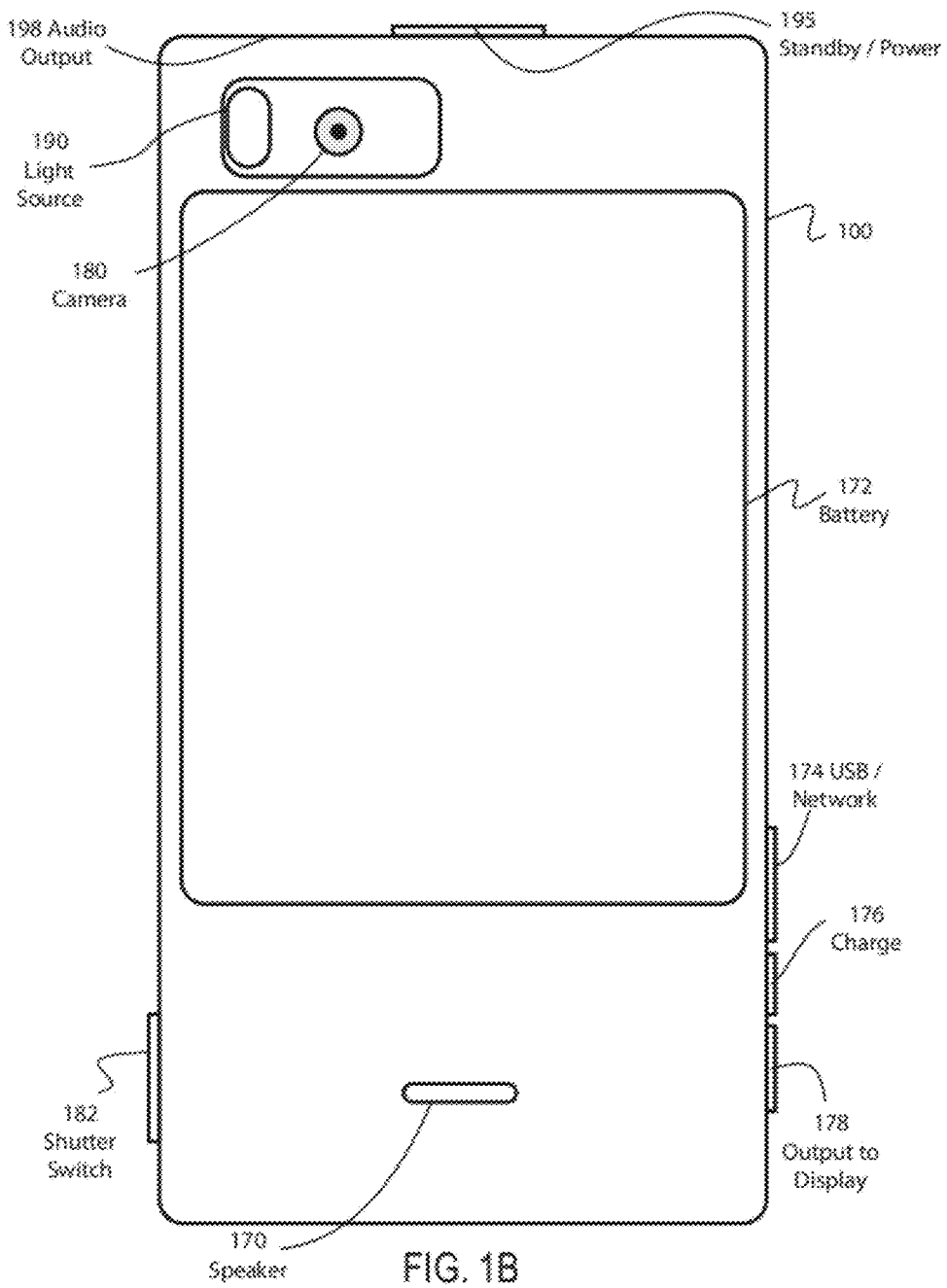
FIG. 1B provides an example of the layout of the rear side of a Motorola Atrix telephone.

Now a biometric mobile device and method of collecting, matching and ranking identification data will be described with reference to FIGS. 1-11D. Referring first to FIGS. 1A and 1B, there are shown the respective front and rear sides of a typical intelligent mobile telephone or other device 100. Such an intelligent telephone will be used by way of example and may be a Motorola Atrix telephone using Android 2.2, Apple's iPhone using iOS or other platforms/operating systems. An advantage of such a telephone is that it may run applications as a special purpose data processor. Moreover, it may comprise special data input devices including a camera for, for example, collecting fingerprint and iris/cornea data and for collecting, for example, bar code identification and DNA specimen data. Such special data input devices may be integrated into the device or connected to the device using a cable or a wireless technology such as Bluetooth. It may comprise an integrated GPS system for collecting location data, an internal day and time clock for capturing event time data. It may comprise a touch screen 110 for collecting four or five fingers of fingerprint data, a physical or virtual keyboard for key entry of weight and height data and the like. All of these are examples of biometric data. Biometric data as defined in this application comprises any data or information that may assist in the identification of an individual, a human body, an animal, or remains, living or deceased, including data such as name, weight, height, fingerprint, iris, cornea, DNA, dental structure, vascular structure and the like which may be unique or may help to limit the identity. For example, a clear fingerprint and DNA profile data are among data that are usable forensic data that may uniquely identify an individual. On the other hand, there may be many individuals that have a height of 200 cm or 6 feet but such data may tend to limit an individual among the population of possible individuals. Moreover, data may be dynamic as an individual may grow in weight or lose weight over time. In a similar manner it may be preferable to utilize date of birth rather than age because age increases over time.

Location data are geographic in nature and so may only indicate the presence of an individual at a given location for a period of time. Location data may be utilized in conjunction with a remotely accessible geographic information system (GIS) such as ArcGIS or other products by ESRI, or an alternative system such as open source software utilizing Open Street Maps data, to display maps or other data as a function of geographic coordinate corresponding to the location of data collection points, found remains, a victim or piece of evidence, or a site of a disaster. Such maps may be displayed using the device's display or touchscreen 110, shared with other users or devices using a wireless or wired communication interface (not shown) or stored to or retrieved from a computer server or database. Maps may be created by such GIS showing the locations of these objects together with other geographic or physical features such as topography, bodies of water, roads, utilities such as power and water lines, streets, and buildings. These maps can, for example, provide aid to disaster or relief workers by providing a summary of structures and content that were present before the disaster, using a local or remote computer database, or multiple databases of either type. It is useful to include a date and time when, for example, weight and geographic location data are stored for a given individual as biometric data, for example, as metadata. If the date or date and time are also available then geographic data can be utilized in, for example, a touch screen display or an external display connected to the mobile device or accessible through a network by the mobile device to indicate changes in a site over a period of time.

Similar reference characters will be used herein to denote similar elements and features. The first numeral will represent where the element first appears, for example, intelligent mobile telephone 100 first appears in FIG. 1. Referring first to FIG. 1A, which may be a front view, there is shown an intelligent mobile device 100 including, but not limited to including a display of, for example, three inches by four inches which may be touch sensitive. This display may be used as a surface for capturing fingerprint data, for example, four rolled or pressed fingers and a thumb at a time or individually from the left or right hand. The surface of display 110 may display a keyboard or may be used to scroll up and down a given list of selectable menu options and by tapping select them. Further intelligent telephone 100 face features may include a microphone 160 for receiving a speaking voice or other sounds and a speaker 170 for announcing speaking voices or sounds of a connected party. Such a microphone may be utilized to record observations made by an investigator at the location of a crime, disaster, or remains, and the mobile device can convert these observations to a digital file in, for example, MP3 format (or convert the speech to text) and cause this file to be stored on a remote server or within the mobile device and associated with data obtained from collected or observed object at the scene. The microphone may also be used to capture sounds such as a voice that can be processed using either a computer processor located within the mobile device or a remote computer processor such as a web or cloud service, or both, to obtain attributes of the sound that can be used to query a local or remote computer database to identify, for example, the person who spoke. Settings 120 provides a means of changing settings of the telephone or software applications stored on the device such as volume control. Home 130 is a key used to access home screen features while Back 140 takes one back to an immediately previous display screen. Search 150 initiates a search. Other intelligent telephones may comprise joystick controls and click features for navigation to and selection of menu items.

FIG. 1B represents the back side of an exemplary intelligent telephone including a camera 180 whose captured image may appear on the display screen 110 of FIG. 1A. In this manner, a photograph may be captured of a processed fingerprint, an iris, cornea, vasculature structure or other characteristic of an individual such as a scar, mark or tattoo. The camera may be located on the front side, or multiple cameras may be implemented. The mobile device may utilize an infrared or ultraviolet light emitting diode (LED) in order to illuminate a scene, such as a portion of an individual's skin, with light having specific wavelengths in order to obtain information such as vascular structure within the skin or details of the iris. A large area 172 may be provided for a battery to power the device 100. Multiple batteries may be utilized with a mechanical or electromechanical mechanism to allow a discharged battery to be removed and replaced with a charged battery without interrupting the device's operation, a process commonly called "hot swapping." External jack 174 may be a USB port or network connector for a memory card or an input device such as an external fingerprint collector or a lab-on-a-chip type of DNA specimen analysis or mass spectrometry data. Charge 176 may be provided to charge the battery 172 or operate the device using a separate source of electrical power. Output 178 may provide an output to an external display such as a larger television or personal computer display. Shutter switch 182 operates the camera 180 which may capture both still images and movies. To capture images in the dark, a light source 190, for example, a selective LED array, may be provided, which as previously noted may produce visible, infrared, or ultraviolet light, or a combination thereof. Settings 120 may be used for the selection or shutter switch 182 adapted depending on the light selected for a given application. Moreover, audio input/output 198 may be provided to, for example, provide audio to an external speaker or to enable the use of a headset containing, for example, ear phones and a microphone.

There may be three or more alternative means for incorporating fingerprint scanning and verification into a mobile telecommunications device 100. Recently, a Motorola Atrix 4G intelligent telephone has been announced with fingerprint identification and a virtual keyboard as well as standard camera and GPS features which may be preferable to use of the Motorola Atrix telephone. With respect to the Motorola Atrix telephone, by way of example, and, referring to FIG. 1B, a first alternative is to adapt the Atrix having a universal serial bus, to incorporate a shell attached to the base on the reverse, proximate USB port 174 for housing an AuthenTec (or equivalent) fingerprint scanner for connection directly to the micro-USB 2.0 port via an intermediate adapter or a native USB solution via, for example, a 90 degree or other angled connector (so that the build-out shell is not overly obtrusive). The shell may be located, for example, between the speaker 170 and the port 174 and comprise a substantially flat housing so as not to interfere with speaker 170. The shell may further house a small USB hub for supporting multiple devices and for external storage. Fingerprint digitization and verification is an inherent feature of AuthenTec's offerings. A second alternative is to provide another USB fingerprint scanner known in the art. The alternative USB fingerprint scanner may consume additional power than the AuthenTec device and require additional system programming. However, a fingerprint software/driver library for Linux is available, known as fprint, and this may be ported to Android or equivalent operating system. A third alternative is to adapt existing camera 180 for capturing fingerprints. A multiple exposure method may be used to capture a complete image and known verification software may be used to provide feedback to a user that a fingerprint has been sufficiently captured.

The shell discussed above may also incorporate a known so-called pocket reader for reading animal radio frequency identification (RFID) tags. These are covered by international standards, operate/receive at 134.2 kHz or other assigned frequencies or frequency ranges, and read a tag such as a fifteen digit international tag. An embedded tag may broadcast and the pocket reader receive and report, for example, an animal's vital signs such as body temperature, heart rate, respiration, blood pH, blood sugar, blood pressure, neuron, muscular, or neuromuscular signals, or other measurements or values computed from such measurements. These are known circuitry which may be incorporated with a separate antenna into the shell and connect to the USB port 174. The RFID tags can also be used to tag shipping containers or other packages or objects to track shipments for applications such as customs, intelligence and counter-terrorism, and law enforcement, and to track packages either domestically or internationally as they are in transit. Such tracking can include measurement of environmental parameters such as temperature, humidity, air pressure or altitude, solar insolation, and geographic coordinates such as latitude, longitude, or any equivalent measurement using another coordinate system. A mobile handheld device such as described herein has high utility in such applications because of its multifunctional capabilities, which can be easily modified by the substitution, update, or addition of software components (typically called an application herein), upgrades to the operating system or system utilities, and its compact size. The mobile handheld device can function as a data gathering system to obtain current or recorded data from, for example, shipping containers.

Figure 2:
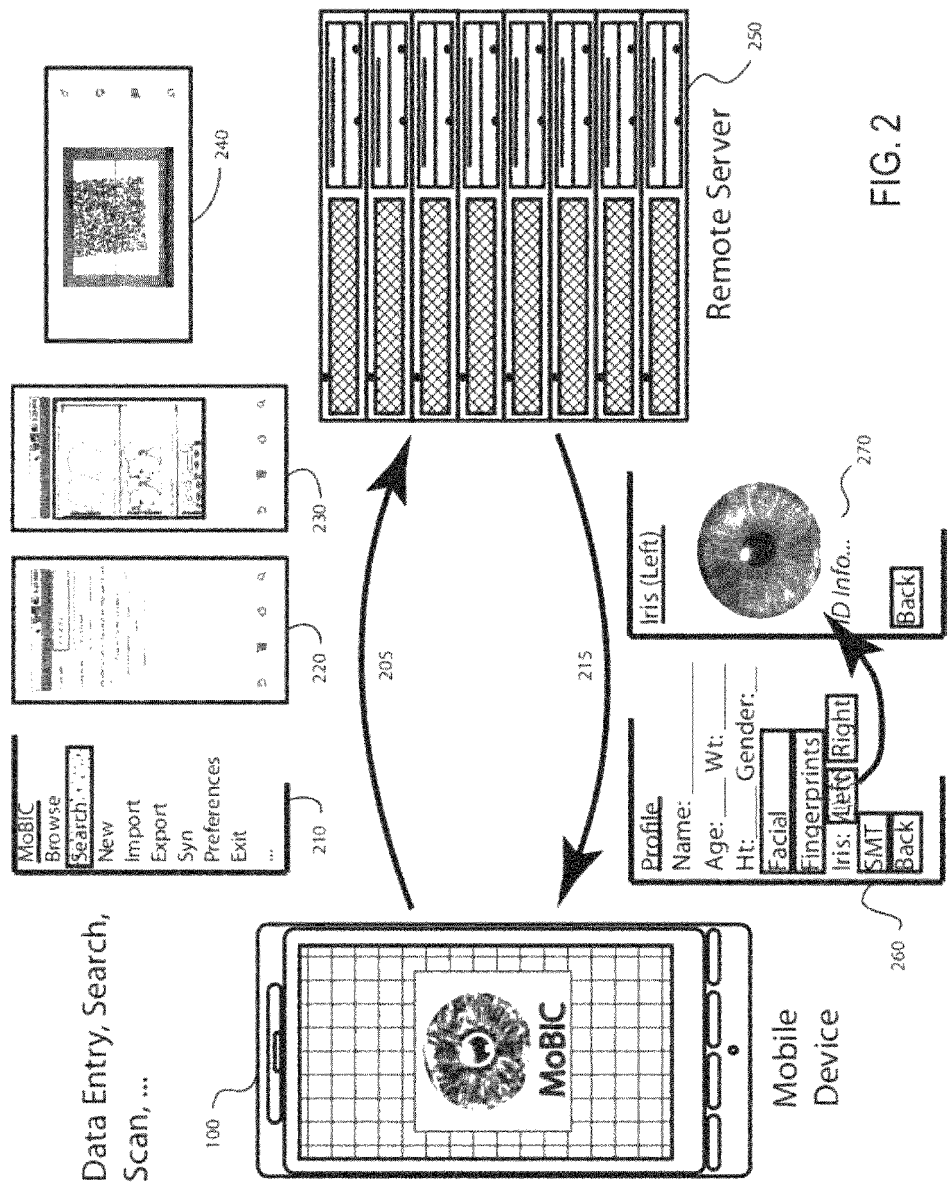
FIG. 2 provides a system block diagram showing an intelligent mobile biometrics device 100, a plurality of exemplary screen displays 210, 220, 230, 240, coupled via a communications interface 205, 215 to a remote server 250 or other cloud server whereby biometric data may be matched and iris scan or fingerprint data matching screens 260, 270 may result that help identify input biometric data to identity data for an individual human or animal, body, or body part.

Now, with reference to FIG. 2, the interaction of an intelligent biometric mobile device with an external server may be described for individual identification. Biometric mobile telephone device 100 is shown communicating with a remote server 250 via a forward link 205 and a reverse link 215 which may be wireless, wired, satellite, cable, fiber optic or other link or composition of such links known in the art. Remote server 250 may be secure and links 205 and 215 may be secured, for example, encrypted links and the server password and key protected as is well known in the art. Links 205, 215 may be internet, extranet, intranet or other communications links.

In a forward direction above link 205 are shown an introductory main menu screen 210 (also shown in FIG. 4A) for a mobile biometric data collection method whereby one may browse, search, input new, import. export. synchronize (sync), establish preferences (settings) and exit. For example, a user of device 100 may create, edit and delete profiles and associated meta-data for human bodies or animals. Synchronization may be utilized, for example, to upload or synchronize data stored within the mobile device with a remote database or an external device such as a hard disk drive connected to the mobile device using the USB or a network connection, either wired or wireless. For, example, synchronization could utilize a remotely accessible network storage device such as one available through the Pogoplug data service or a cloud service provider. Screen 220 (also shown in FIG. 8E) demonstrates the automatic collection of GPS location data, and while not shown, mobile device 100 typically comprises an automatic time, date clock for time stamping photographic, location and other biometric data, for example, as metadata.

Screen 230 (details shown in FIG. 8D) represents a typical screen for characterizing an individual profile having certain characteristics in a manner known, for example, in disaster and crime victim identification processes, for example, according to Interpol. Screen 240 (details shown in FIG. 8C) represents the collection of a two dimensional bar code which may, for example, represent a DNA profile while a one dimensional bar code may represent identification data for an individual. This screen 240 may be shown on display 110 and may be captured via camera 180. Likewise, camera 180 may capture an image of an iris, a cornea, a vascular structure or heat signature of a face or other body part, a dental structure. a fingerprint or collection of fingerprints, a face, scars, marks, or tattoos, and the like. This captured image can then be used for identification by querying a local or remote computer database. Further screens are shown below return link 215 as comprising Profile screen 260 and, from Profile screen 260, particular details for left iris screen 270 (also shown in FIG. 8B). Remote server 250 may locate a match between all or any portion of biometric data provided and data for a known individual stored at a database of remote server 250 and may comprise one or more computers. The match may be made to, for example, watch lists, access lists, personnel records, criminal records and the like. Using matching algorithms a match to a family pedigree or specific member of a family may be determined, for example, using DNA profile data for family members as described in published U.S. Patent Application No. 2008/0040046 of Feb. 14, 2008, (now U.S. Pat. No. 8,271,201 issued Sep. 18, 2012). The device may utilize the methods disclosed in published U.S. Patent Application No. 2010/0138374 of Jun. 3, 2010, (now U.S. Pat. No. 8,301, 392 issued Oct. 30, 2012), to suggest that data be obtained from specific family members or to assist the user in choosing what data to collect. A match may be obtained for a partial print. A probability may be calculated by weighting various parametric biometric data to determine the identity of an individual and that identity returned to mobile device 100 and utilizing either population statistics obtained from a sample population or known probabilities. The process will now be further explained with reference to exemplary screens.

Figure 3A:
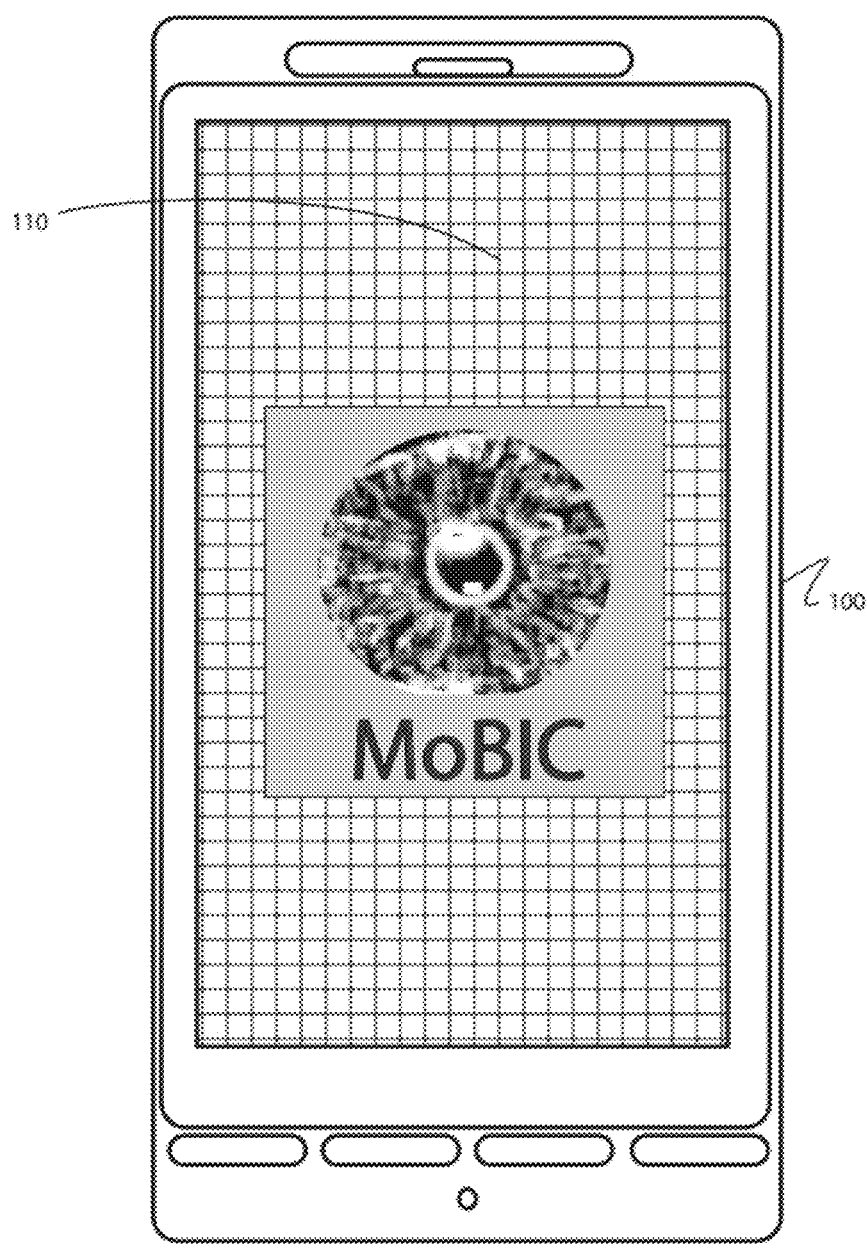
FIG. 3A provides a further view of a biometric mobile device 100 having a mobile biometric information collection application running thereon as a computer implemented method and/or special purpose data processor for identifying an individual to collected biometric data.
Figure 3B:
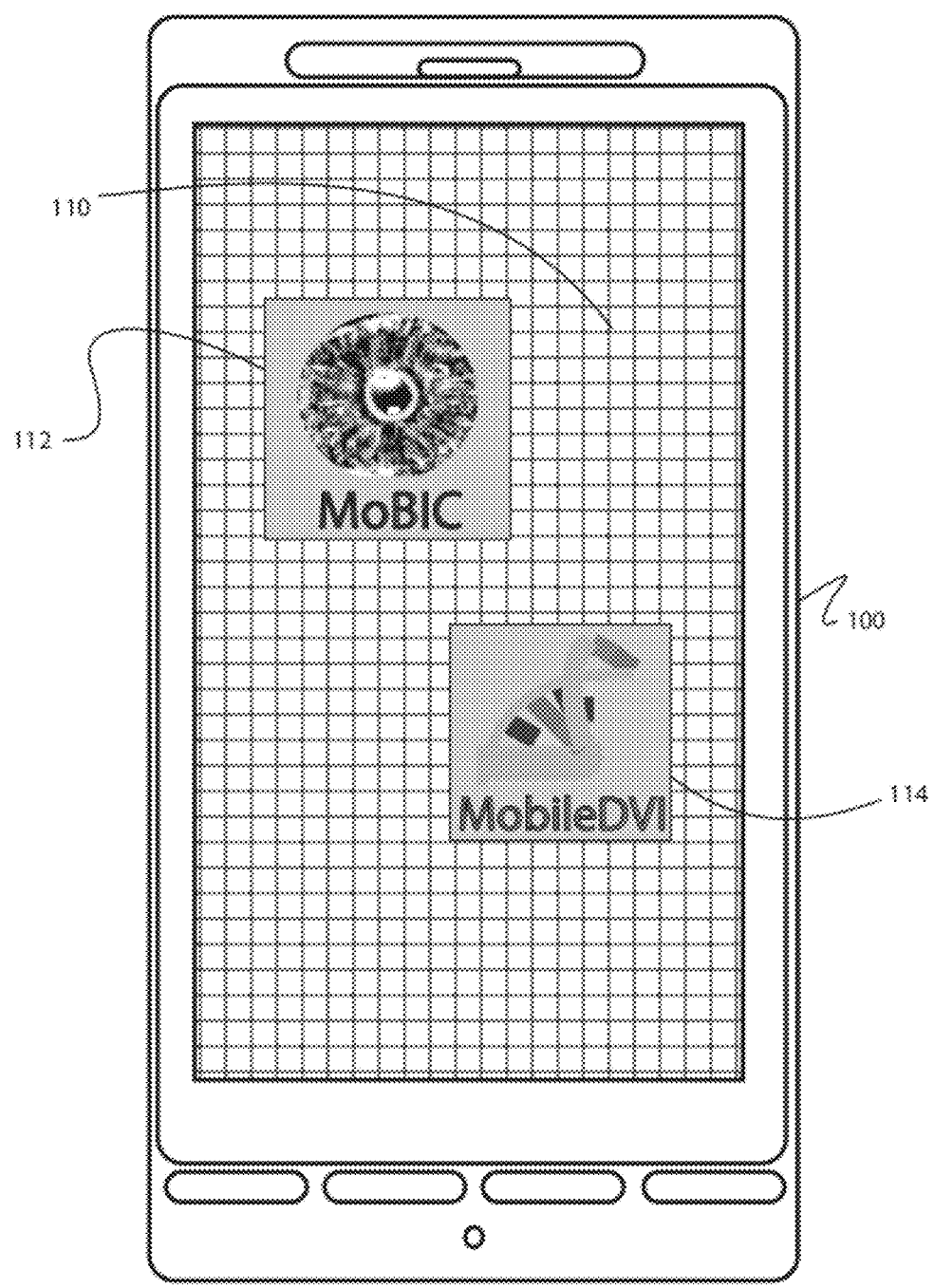
FIG. 3B provides a further view of a biometric mobile device 100 having first and second applications for biometric data collection (MoBIC) 112 and disaster victim identification by DNA specimen (MobileDVI) 114 which are selectable by touch screen or by use of a joystick and click.
Figure 3C:
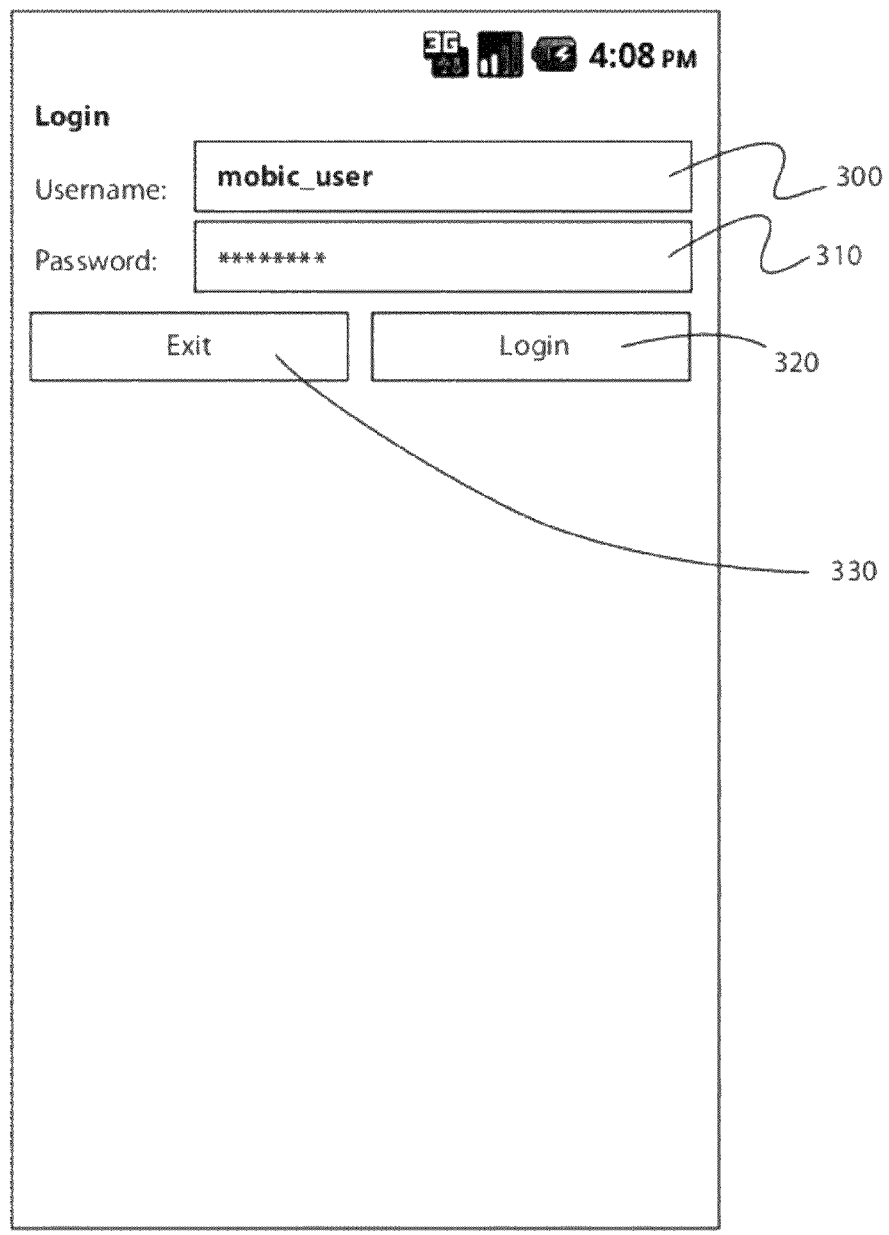
FIG. 3C provides a log-in screen for MoBIC.

FIG. 3A depicts, by way of example, an intelligent mobile device 100 showing on its display 110 an example of applications software referred to herein as MoBIC or mobile biometric information collection (and identification). FIG. 3B provides a further view of a biometric mobile device 100 having first and second applications shown on its display 110 for biometric data collection (MoBIC) 112 and for disaster victim identification by DNA specimen (MobileDVI) 114 which are selectable by touch screen or by use of a joystick and click of an exemplary intelligent device 100. Another application can be made available by placement of an icon representing it on the screen in a similar manner. For example, a MobileLSD application can be made available that implements DNA mixture deconvolution methods such as those described in U.S. Pat. Nos. 7,162,372 and 7,672,789, using either a computer processor located within the mobile device or a remote computer processor such as a web or cloud service. FIG. 3C provides a log-in screen for MoBIC where Username: 300 provides for user name entry; Password: 310 provides for password entry; Exit 330 allows a user to exit and Login 320 permits logging in if the user name and password are entered correctly. Other user authentication methods, as are well-known in the art, may be used, or no authentication may be required.

Figure 4A:
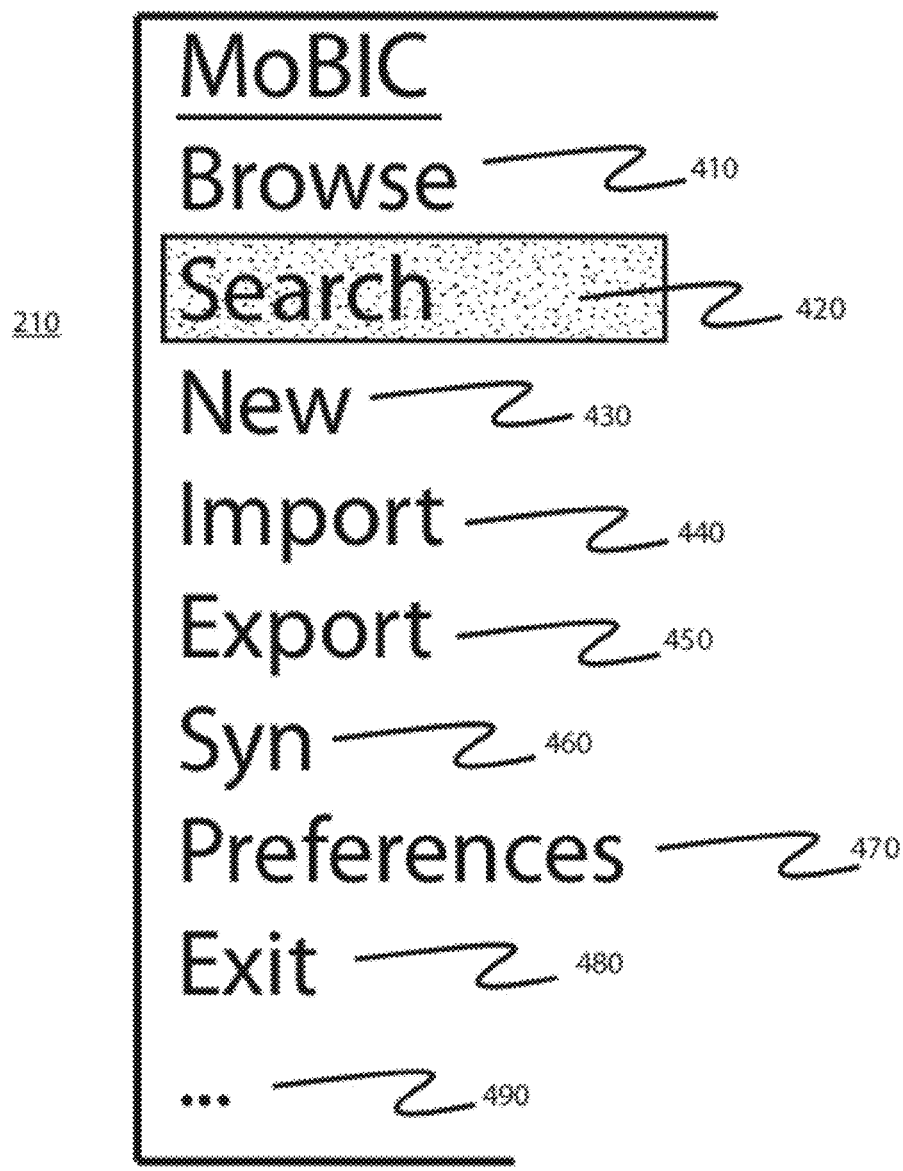
FIG. 4A provides an example of an initial menu screen for a MoBIC application including various selectable functions including browse and search, import and export functions.
Figure 4B:
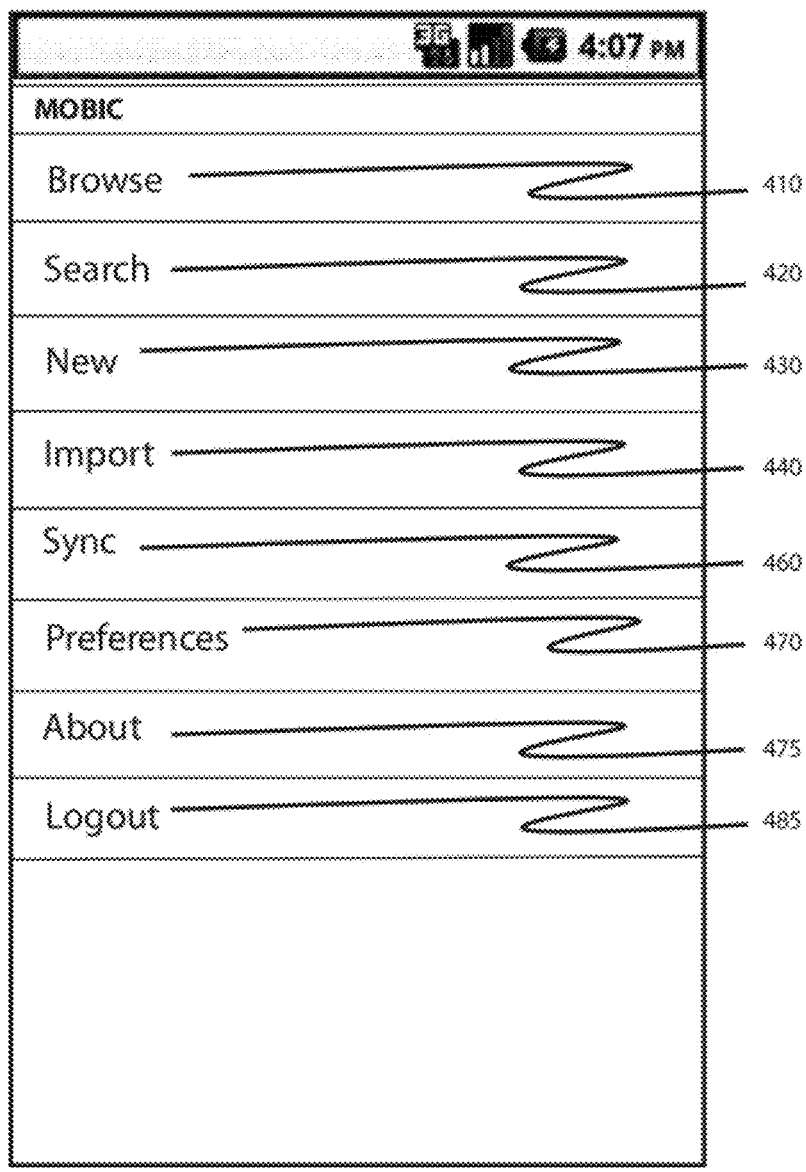
FIG. 4B provides an alternative example of an introductory menu screen for a MoBIC application including various selectable functions such as browse and search, import and about.
Figure 4C:
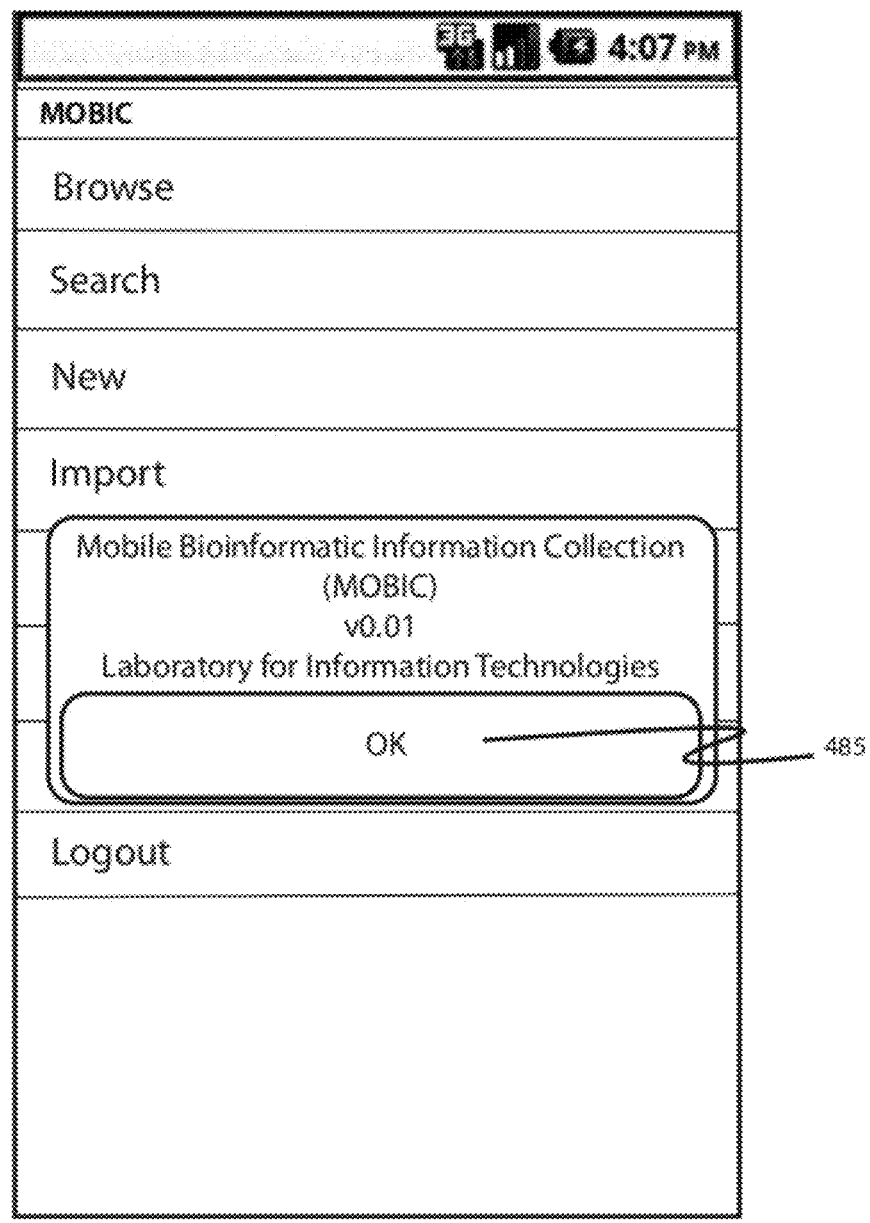
FIG. 4C provides an example of a screen showing access and an "OK" selection 485.
Figure 4D:
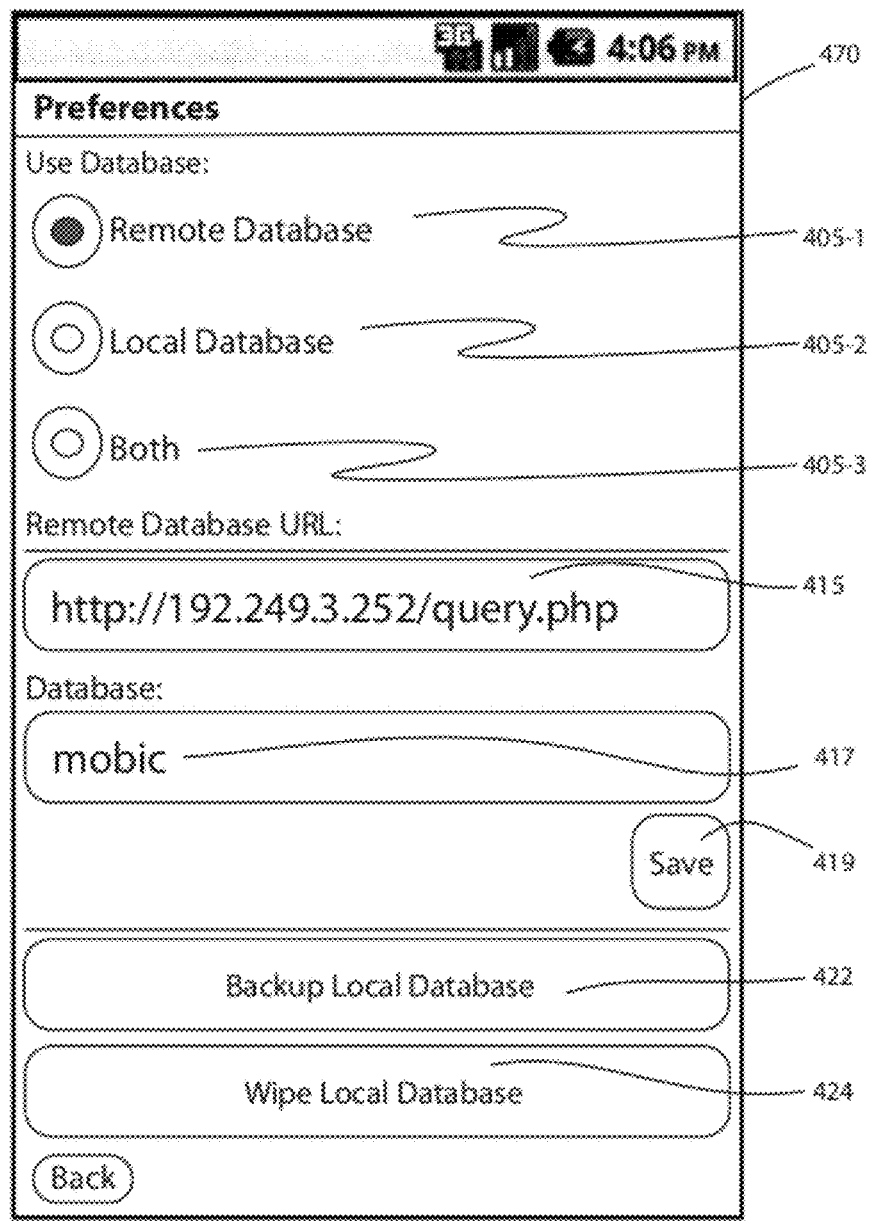
FIG. 4D provides an example of a preferences screen when Preferences 470 is selected from FIG. 4A or 4B.

FIG. 4A provides an example of an introductory menu screen for a MoBIC application including various selectable functions including browse and search, import and export functions. FIG. 4A is an example of a main menu for a mobile biometric data collection application program making mobile telephone device 100 a special purpose data processor. The depicted main menu may comprise, for example, a browse selection that may be scrolled to or otherwise displayed and selected by joystick and click or by touch screen entry. Browse allows a user to view data previously entered locally stored data or data of a remote database such as that of remote server 250. Search 420 provides a search feature for searching for particular biometric data and locating/narrowing a search to a particular possible individual match for biometric data entered. New 430 provides a selection for entering new data about an individual, remains, specimen, or a known human body or animal. Import 440 provides a selection means for importing biometric data from another device or server such as server 250 or reading, for example, a barcode while Export 450 provides a means for exporting biometric or other data by, for example, e-mail, posting to a secure web site, or SMS, using methods well-known in the art. Synchronize or syn 460 is used to synchronize one database to another or one file or collection of files to another so that the most recent data are stored in both. Preferences 470 provides a means for establishing preferences for settings such as camera settings, audio volume settings, font size settings for display 110 and other user preferences for operating intelligent telephone device 100. Exit 480 provides a means for exiting the MoBIC application. Other selections 490 may come to mind of one of ordinary skill in the art for a typical main menu, for example, dependent on device use for fire, police, rescue, military, security or other personnel. FIG. 4B provides an alternative introductory menu screen having About 475 for learning about and Logout 485 replacing Exit 480. FIG. 4C provides an intermediate screen to show that one may actuate OK 435 to access MoBIC after viewing either help or about data or data from another application. Preference 470 are shown in greater detail in FIG. 4D. Selections include, but are not limited to, a database selection of Remote 405-1, Local 405-2 or Both 405-3. The remote database URL is entered in Remote Database URL: 415. The name of the Database 417 is entered and Save 419 saves the selections. There are also selections for backing up the local database 422 and, for example, once backed up, the local database may be wiped at Wipe 424.

Figure 5:
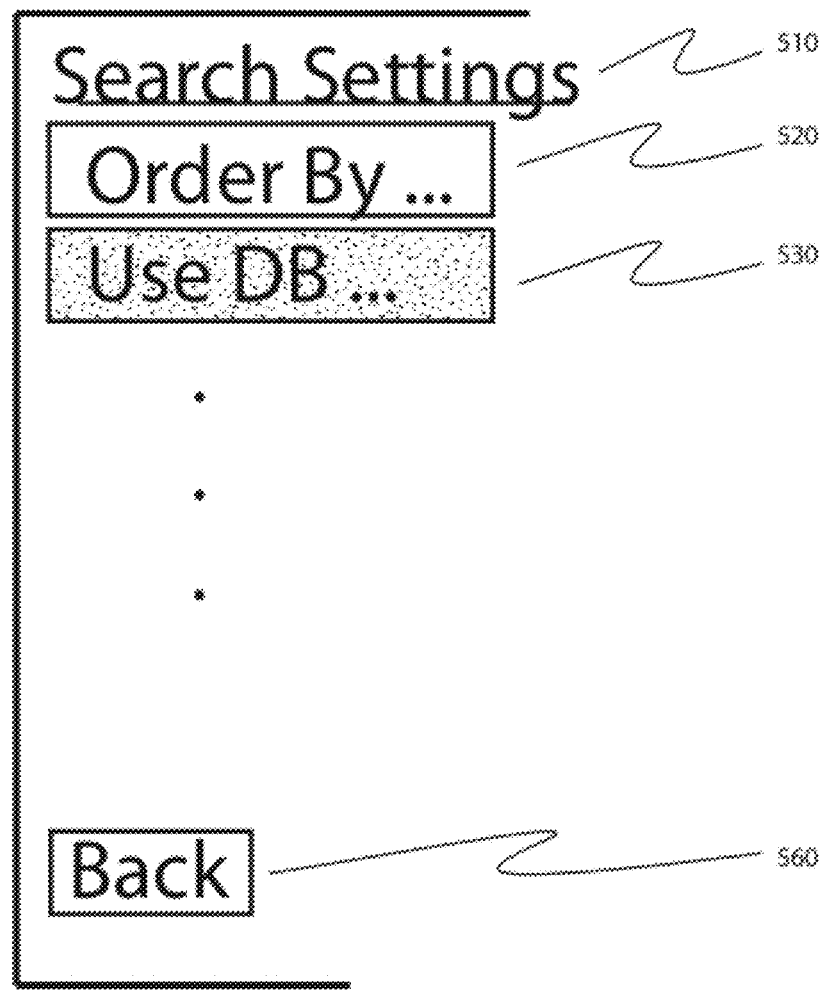
FIG. 5 provides a further menu of selectable options if search is selected from the main menu for mobile biometric information collection depicted in FIG. 4.

FIG. 5 provides a further menu of selectable options if search 420 or Preferences 470 is selected from the main menu for mobile biometric information collection depicted in FIG. 4. Order by 520 is an example of a selection for ordering biometric information in a particular order for a particular human body or animal or collection or with respect to information such as a family pedigree. Order by may be used to control the ordering by the degree or quality of a match to search criteria. One may order by height, weight, age. alphabetical name, date, time, location or other parameter of biometric data. One may also order by the value of a computed quantity such as a likelihood ratio, as discussed in published U.S. Patent Application No. 2008/0040046 of Feb. 14, 2008, (now U.S. Pat. No. 8,271,201 issued Sep. 18, 2012. One may also select a given database to use via Use DB 530. The selected database may be specific to a disaster site, a lab, or a task or application, and may be local, state, federal or international. For example, the database may contain child biometric data offered for storage to a state by one or both parents for identification purposes. It may be local, such as hospital or device local data or other device or external memory device biometric data. It may be federal such as armed forces data collected by the Department of Defense for military personnel, or the Federal Bureau of investigation for missing persons or those involved in federal criminal activity. It may be social network data collected and maintained on social networks and respective databases. It may be business data collected by business entities for employees, for example, during employment physicals. Finally, Back 560 takes one back to the previous screen. Alternatively, in any case where a Back selection is possible, a dedicated Back button provided by the mobile device may be utilized for the same purpose. Alternatively, in any case where a Back selection is possible, a dedicated Back button provided by the mobile device may be utilized for the same purpose.

Figure 6A:
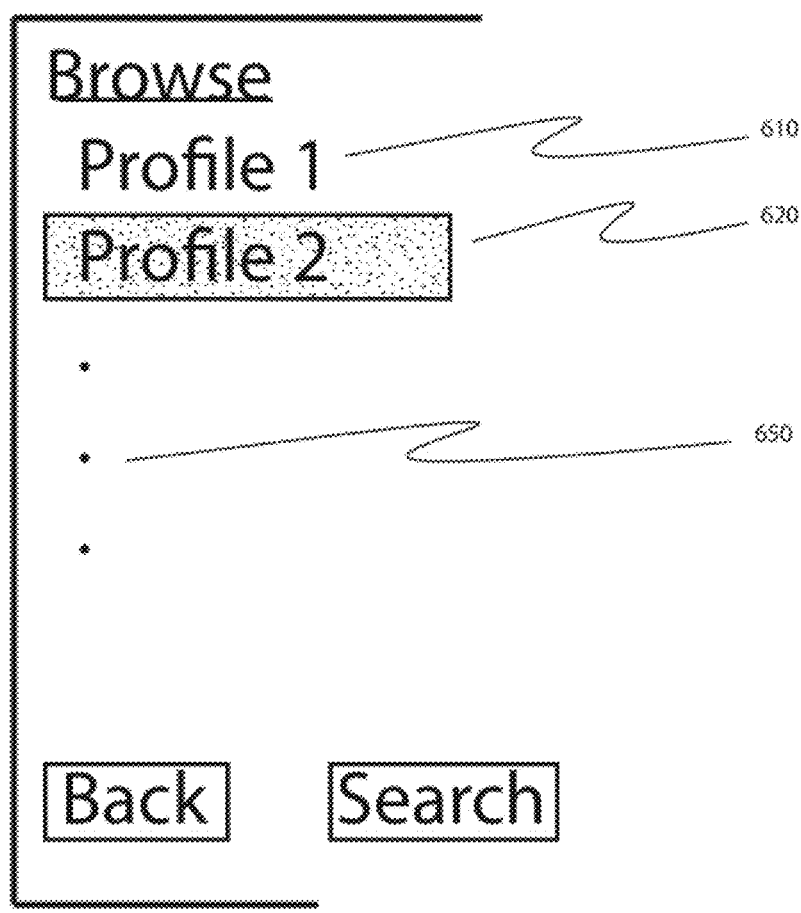
FIG. 6A provides a further menu of selectable options if browse is selected from the main menu for mobile biometric information collection depicted in FIG. 4 for browsing a selectable profile.
Figure 6B:
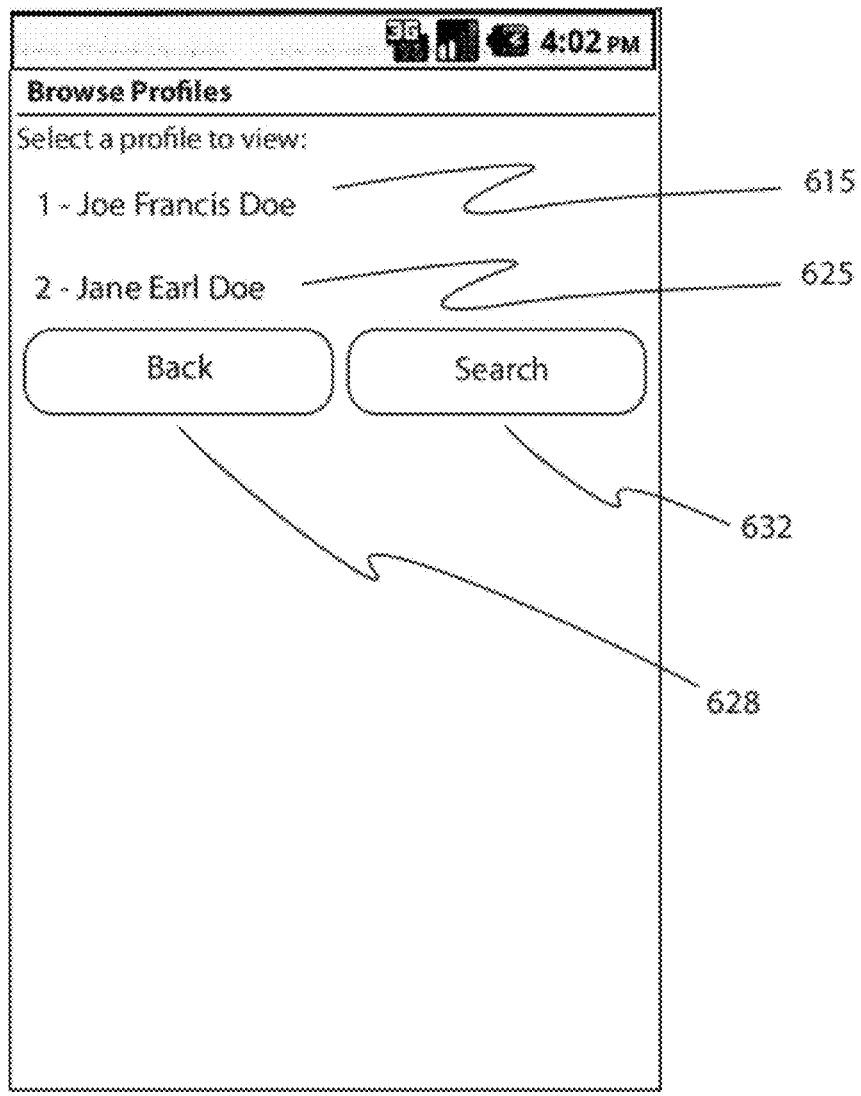
FIG. 6B is an alternative screen to that of FIG. 6A for selecting a profile to view.
Figure 6C:
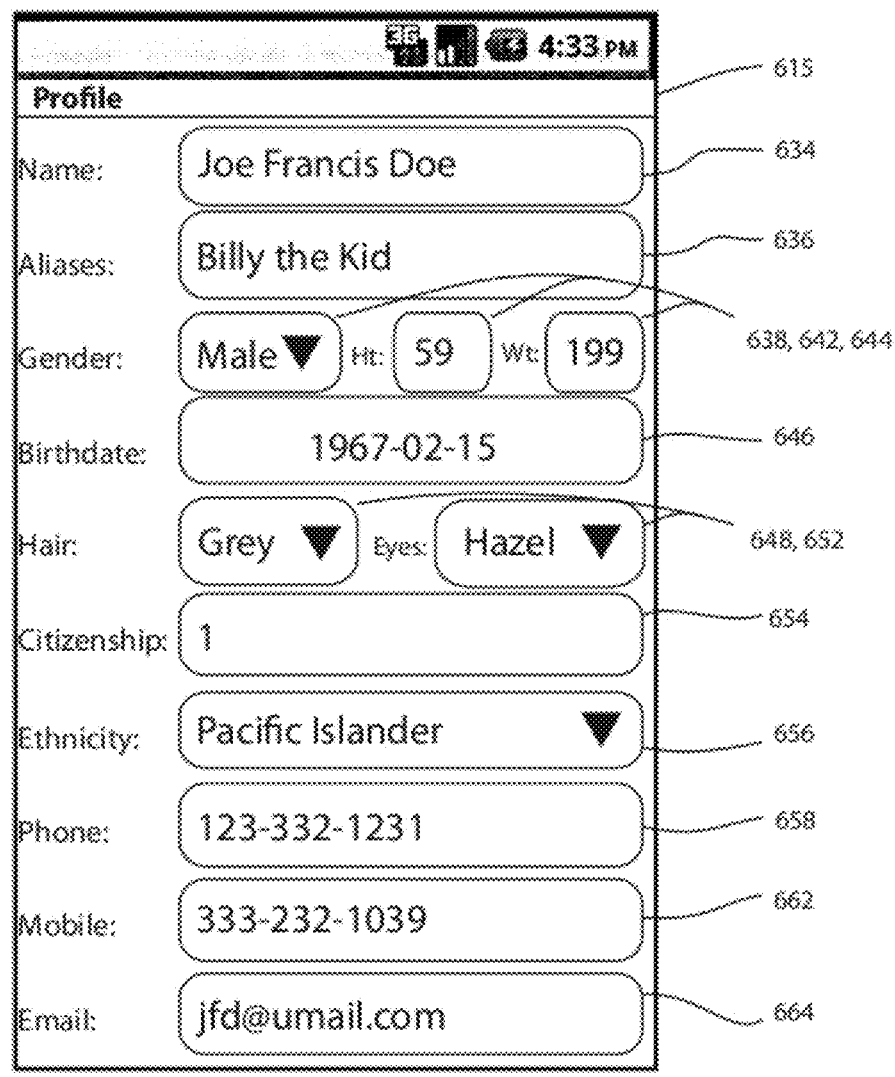
FIG. 6C shows a typical profile comprising a plurality of biometric parameters which may be scrolled to or slid to using a touch screen or joystick and click to change data.
Figure 6D:
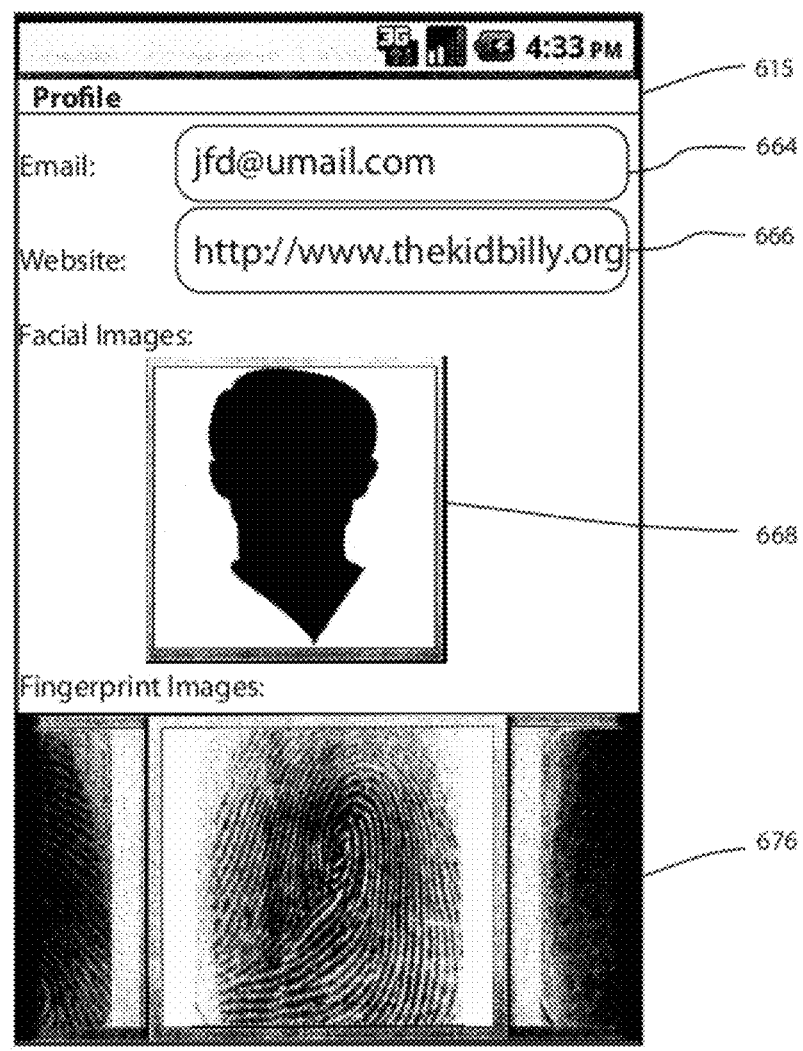
FIG. 6D is a continuation screen for the data shown in FIG. 6C.
Figure 6E:
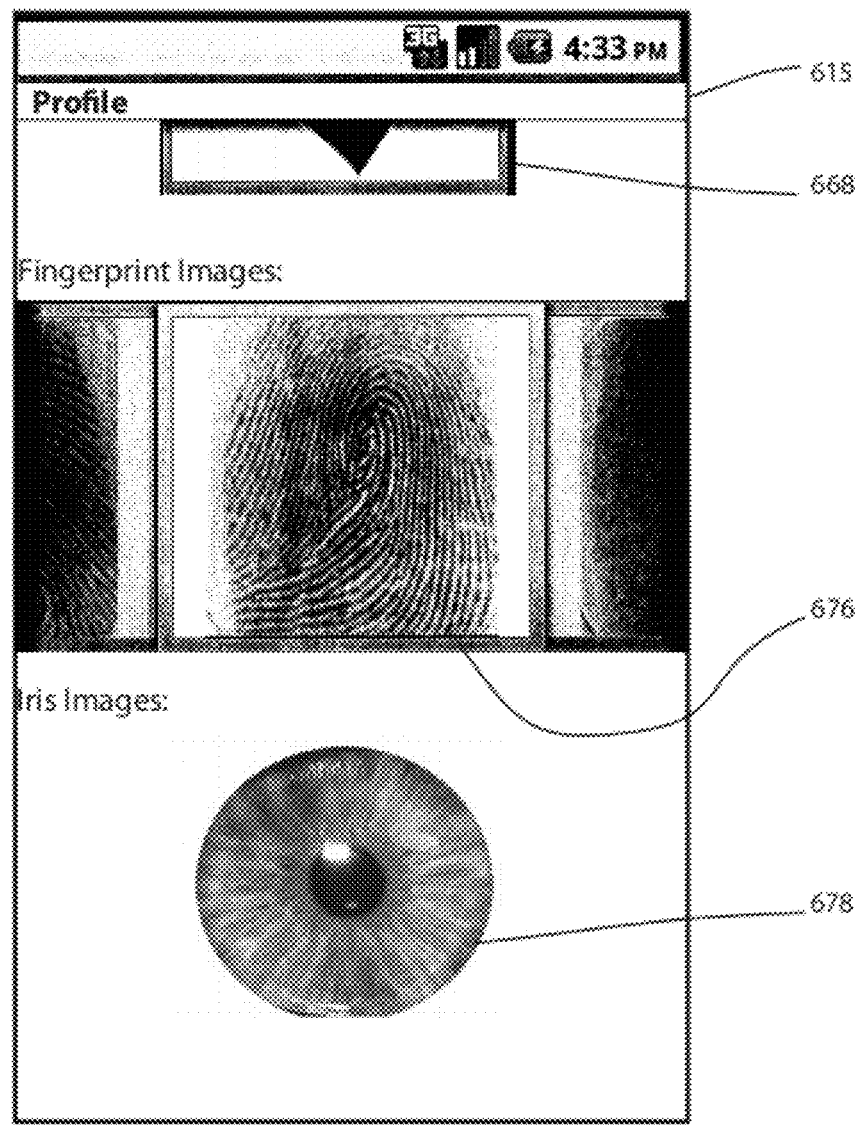
FIG. 6E is a continuation screen for the data shown in FIG. 6D.
Figure 6F:
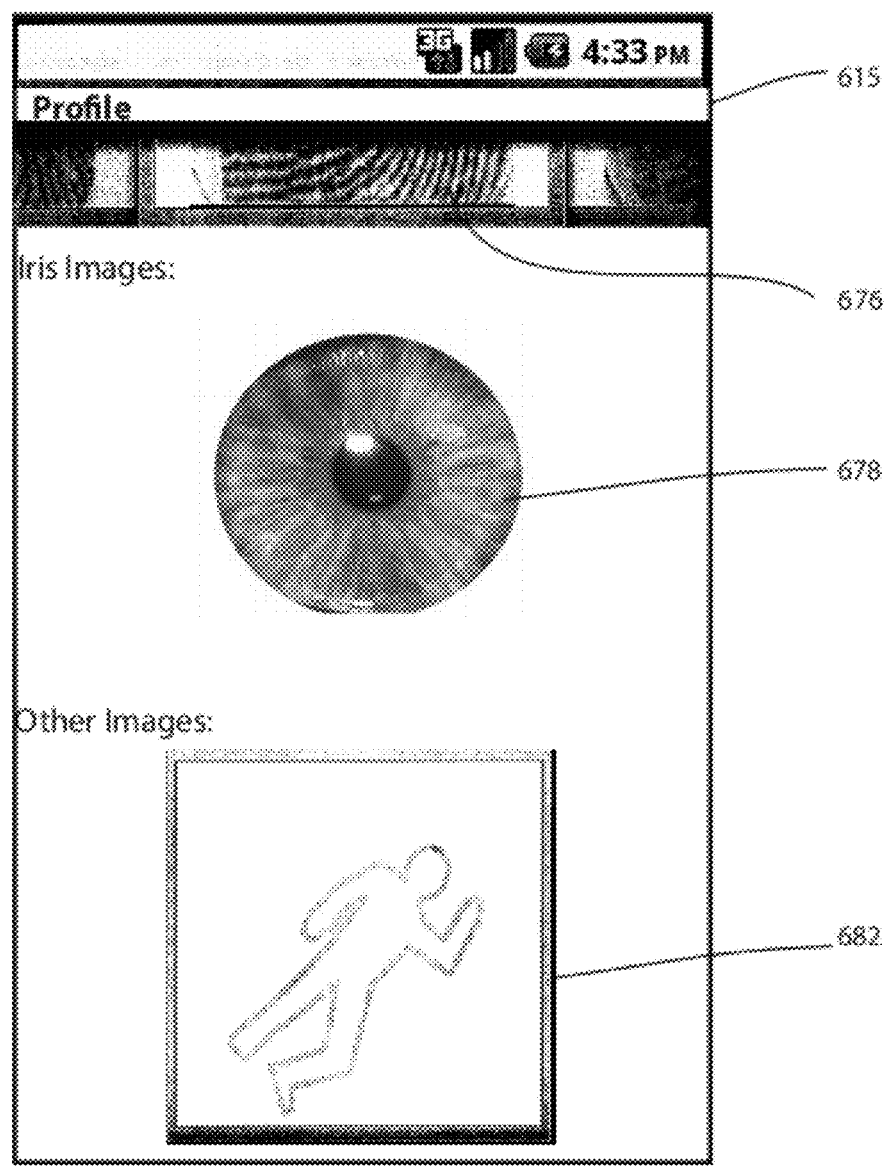
FIG. 6F is a continuation screen for the data shown in FIG. 6E.
Figure 6G:
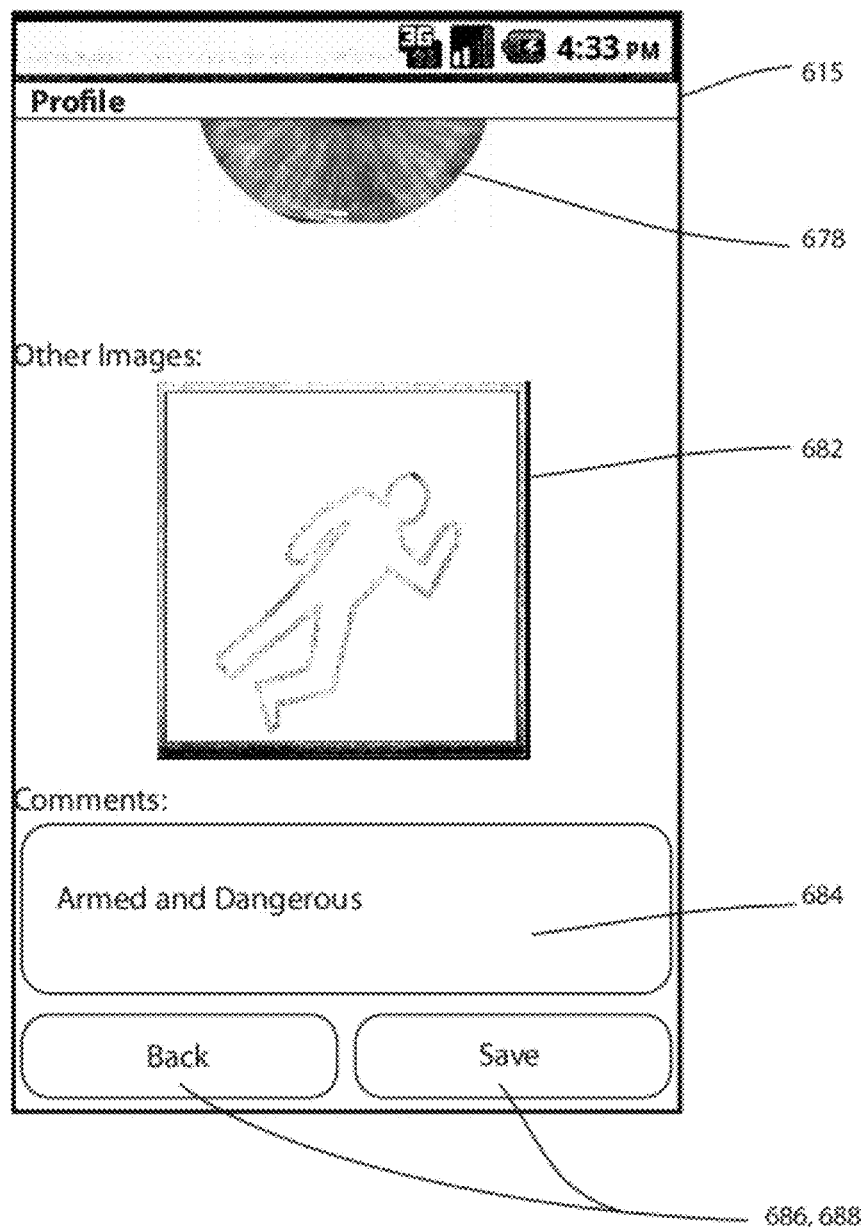
FIG. 6G is a continuation screen for the data shown in FIG. 6F including a comments section.

FIG. 6A provides a further menu of selectable options if browse is selected from the main menu for mobile biometric information collection depicted in FIG. 4. There are shown a plurality of exemplary profiles including Profile 1 610 and Profile 2 620 for biometric information, metadata and other information collected for a first profile. Dots 650 simply represents a plurality of profiles for human or animal bodies that may be browsed in one or another order, accessed randomly or according to a browse through a succession of screens. Search key provides a means of searching the depicted profiles and Back takes one back to the Browse selection screen of FIG. 4. FIG. 6B is an alternative screen to FIG. 6A whereby profile 1 is for Joe Doe 615 or profile 2 is for Jane Doe 625. There are provided Search 632 and Back 628 selections. Assuming a user has selected Joe Doe, then Profile 615 may comprise Name 634, Aliases 636, gender 638, height 642, weight 644, birth date 646, hair 648, eyes 652, citizenship by code 654, ethnicity 656, phone 658, mobile 662 and e-mail 664, as shown in FIG. 6C. The profile may be scrollable and horizontally slidable per FIGS. 6D-6G. FIG. 6D shows additional entries for facial images 668 and fingerprint images 676. FIG. 6E shows scrolling to an iris image 678 (left and right, not shown but to the right). FIG. 6F shows other images 682, for example, a crime scene as to how an individual is found. All images may be dated, time-stamped, and located with metadata. FIG. 6G adds comments 684 and Save 688 or Back 686. Other fields can be added as needed.

Figure 7A:
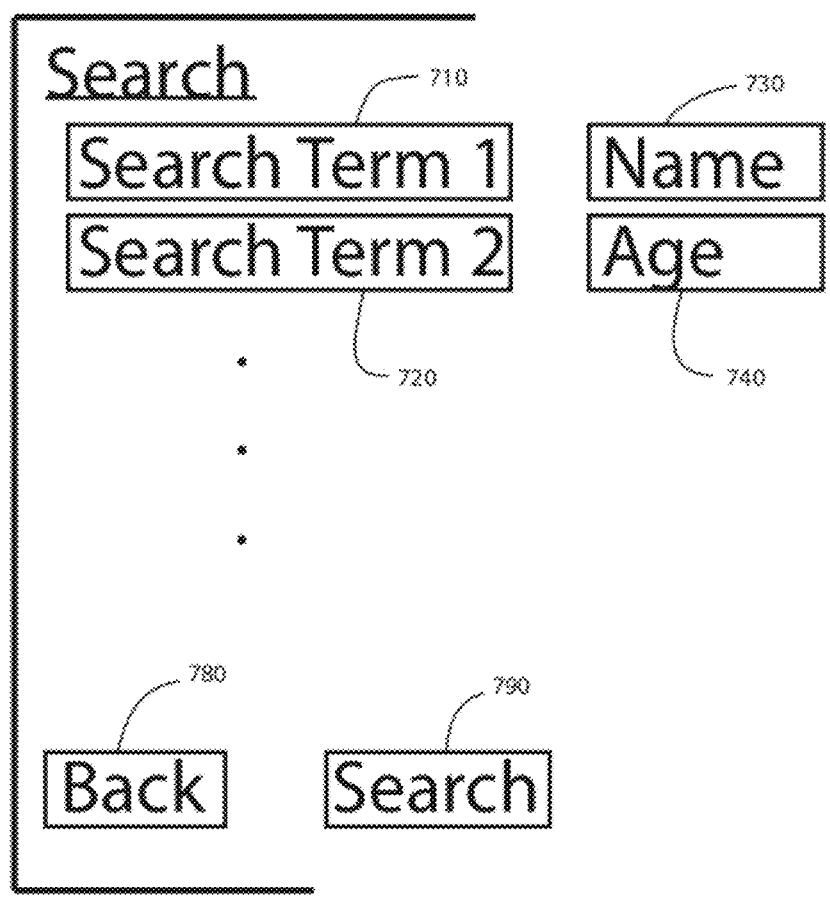
Figure 7B:
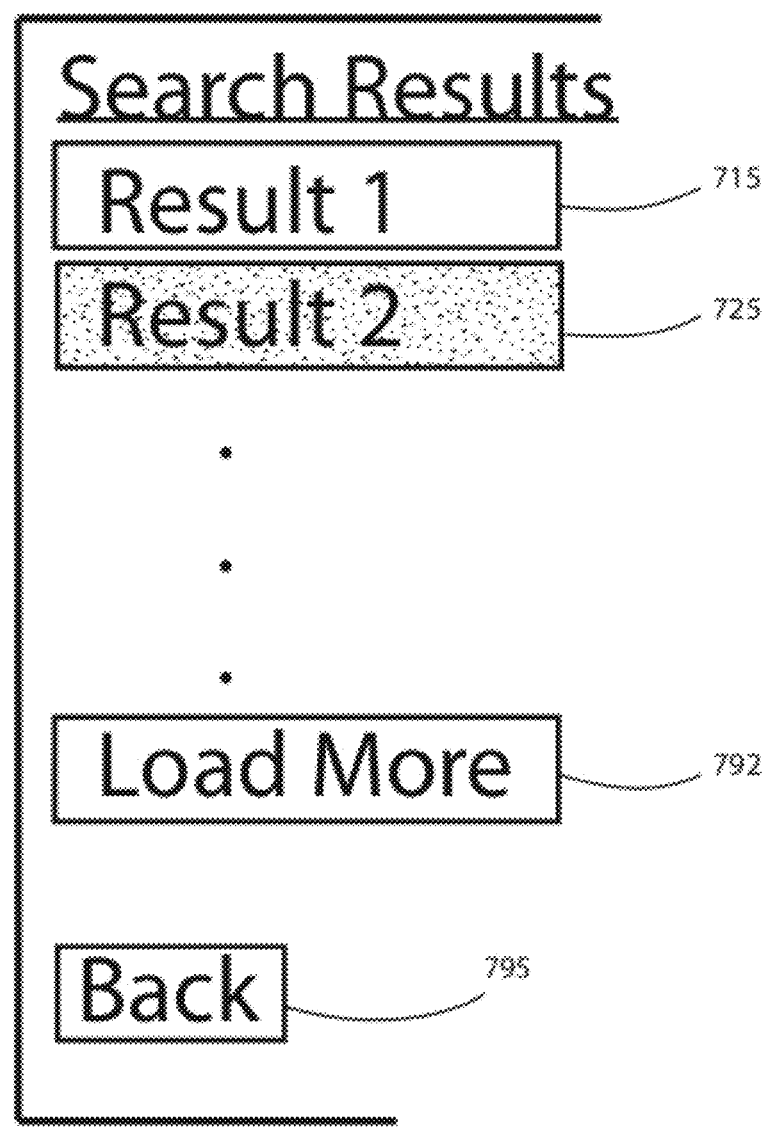
FIG. 7B provides search results as a result of the search of FIG. 7A.

FIG. 7A provides a further selectable menu of options if an "order by" is selected, for example, for a particular database whereby one or more search terms, Search Term 1 710 and/or Search Term 2 720 for a Boolean search are input via a keyboard. not shown, of an exemplary mobile telephone device 100 of FIG. 1. One may search, for example, by name 730, age 740 and the like. There may be many Samuel Jones names but the search by age and other biometric input may limit the search eventually to one such Samuel Jones. Once one has entered search terms and parameters, one actuates Search 790 to begin the search. Back 780 takes one back to the search selection screen. for example, of FIG. 4. FIG. 7B provides search results as a result of the search of FIG. 7A. As a result of a search a ranked or ordered search result list may be presented of the most likely candidate individual to the least likely candidate individual that complies with the search terms and parameters entered. One method of achieving this is given, by example, in published U.S. Patent Application No. 2008/0040046 of Feb. 14, 2008, (now U.S. Pat. No. 8,271,201 issued Sep. 18, 2012). Load more 790 operates to load more, for example, less likely candidate search results to a page and Back 795 takes one back one page to previous search results or to the original search criteria screen of FIG. 7A. For example, a likelihood ratio may be utilized to order a ranked list.

Figure 8A:
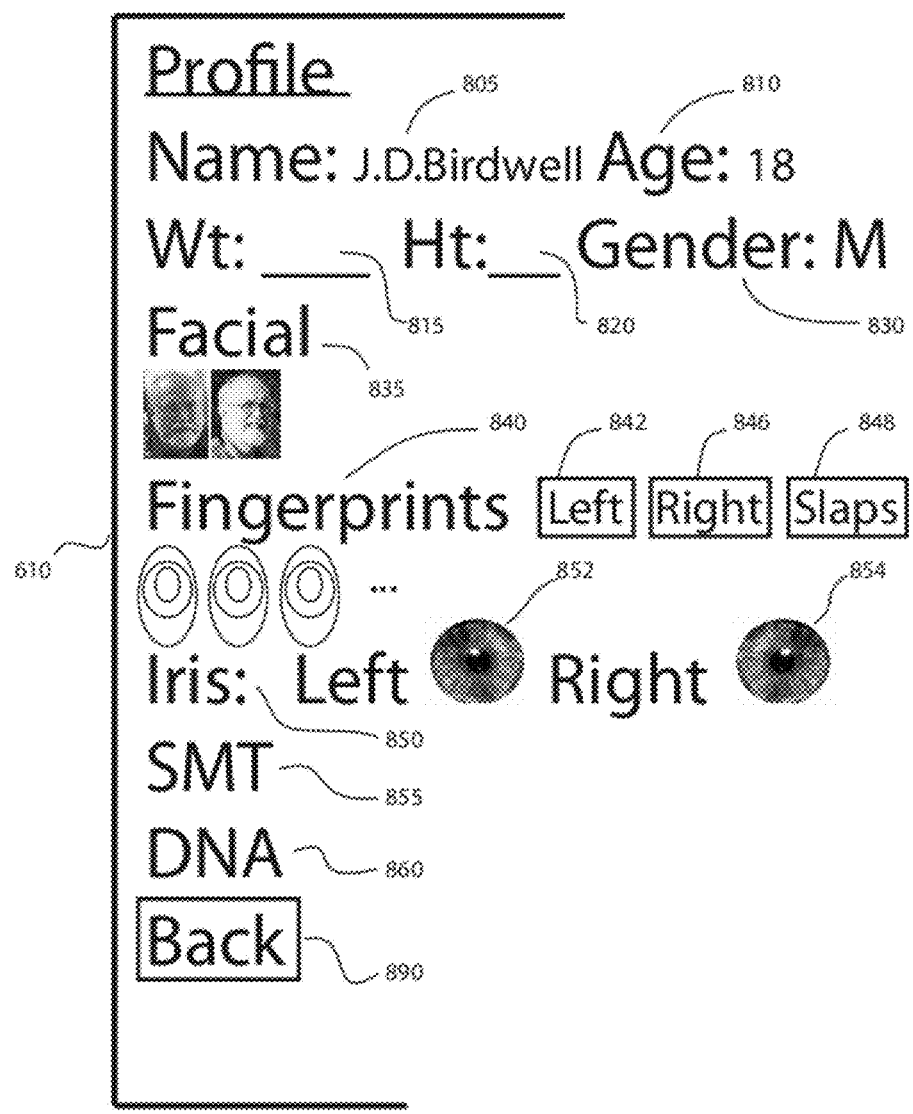

FIG. 8A provides an exemplary profile display screen 610 showing target (or unknown) biometric data associated with an individual having the Name 805 J. D. Birdwell including, for example, besides name, age 810, weight 815, height 820, gender 830, facial 835, fingerprint 840, (Left 842, Right 846, slaps for left and right hands 848 (four fingers each, possibly with a thumb), Iris 850 (cornea), Left 852, Right 854, scars, marks and tattoos (SMT) 855, DNA 860 specimen profile data and the like. This profile of FIG. 8A may be entered as New, Imported, Exported, Searched and Retrieved as a search result and the like.

Figure 8B:
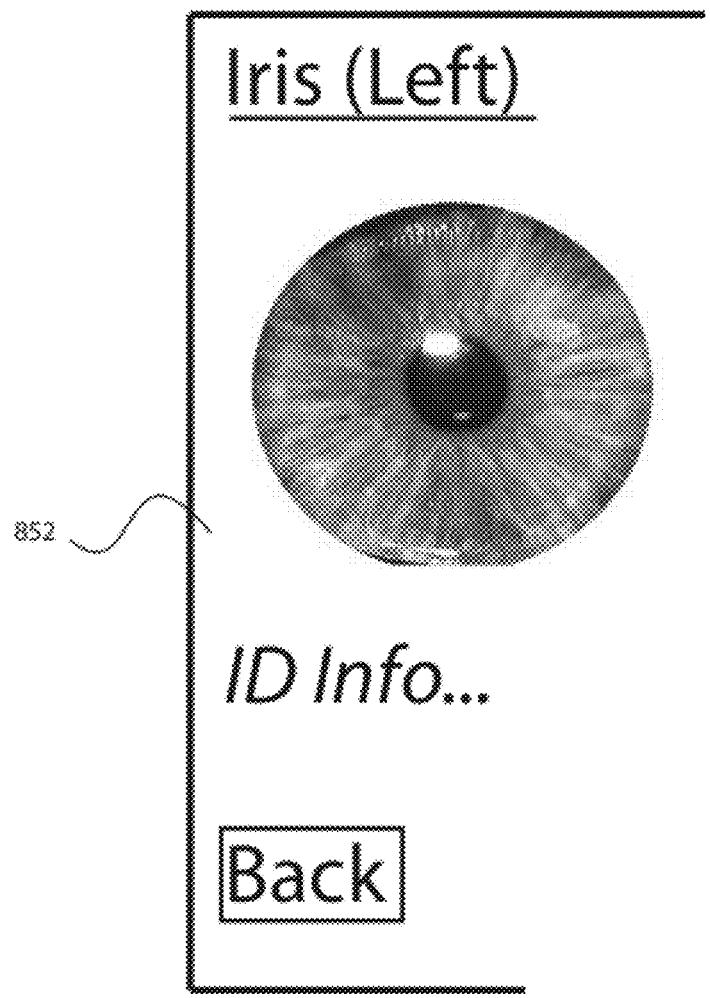
FIG. 8B provides an example of a left iris and the return of identification information thereof, which can be obtained from a local or remote computer database.
Figure 8C:
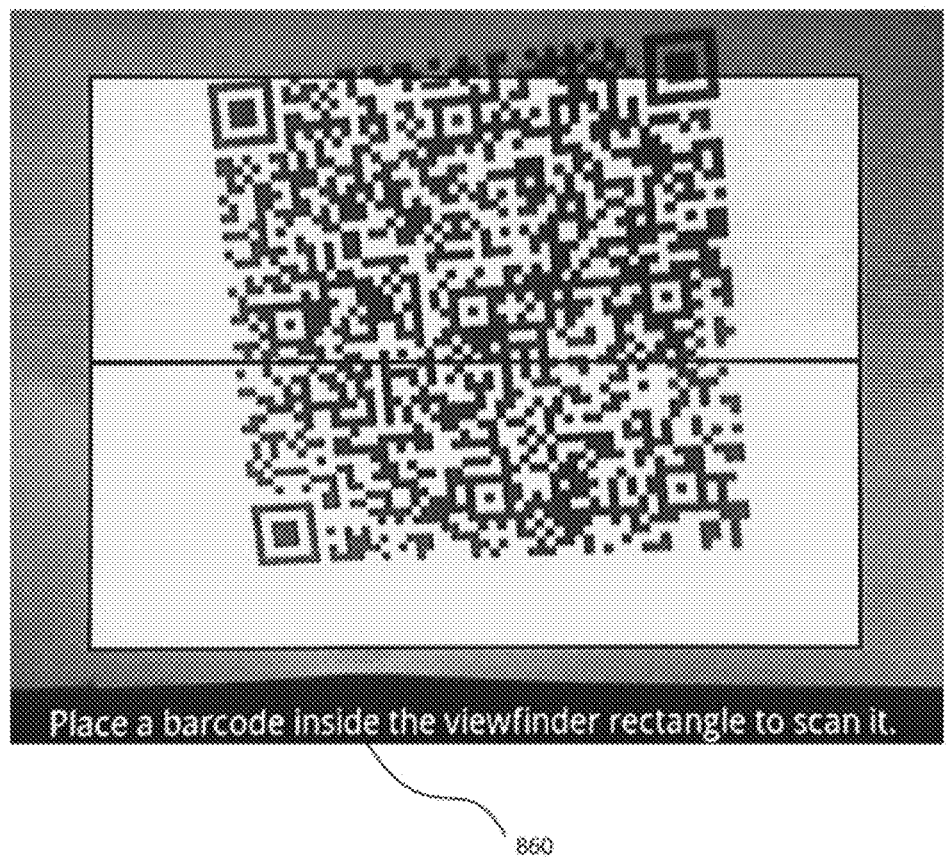
FIG. 8C represents the input of a one dimensional (not shown) identification of a specimen and two dimension bar code (shown) representing for example DNA profile data for a male or female individual.
Figure 8D:
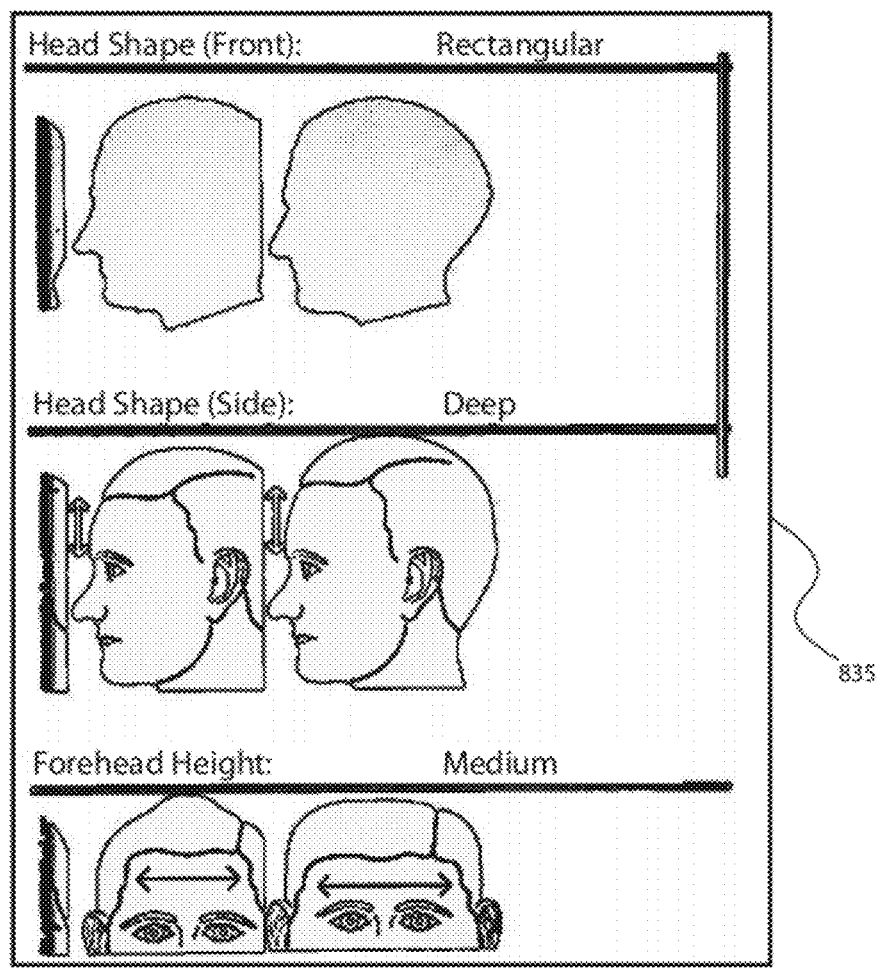
FIG. 8D represents detail similar to that found for an Interpol victim identification report whereby the head shape profile may be typed, selected and input by touch screen or by use of a joy stick and click.
Figure 8E:
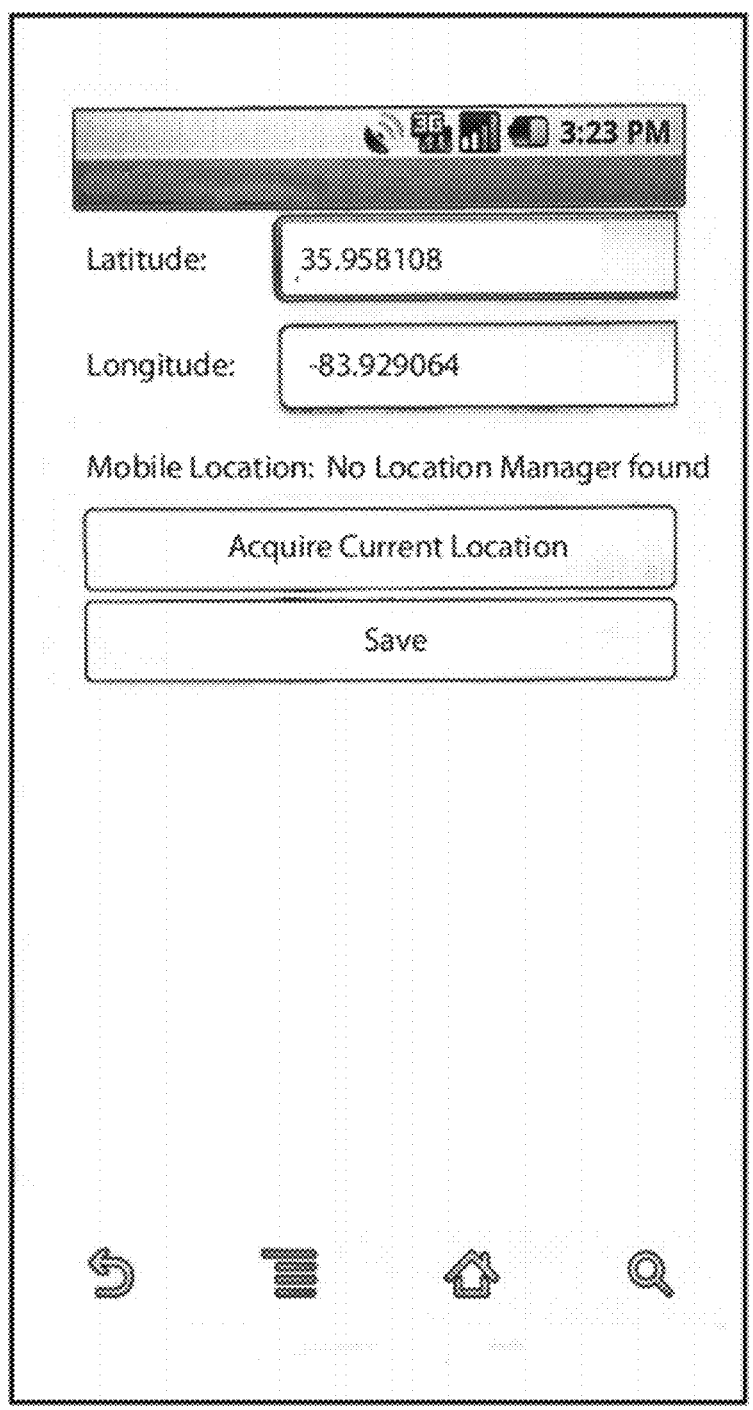
FIG. 8E represents the automatic entry of GPS coordinate data indicative of a location, for example, of an accident or crime scene or current whereabouts of an individual possessing the mobile telephone or other device.

FIG. 8B provides an example 852 of a left iris and the return of identification information therefor. Back takes one back to a previous screen. FIG. 8C represents the input of a one dimensional (not shown) identification of a specimen and two dimension bar code (shown) representing, for example, DNA profile data for a male or female individual. FIG. 8C generically represents the capture, for example, of fingerprint data for a given finger, or slap of four fingers of one hand or the capture of an iris or cornea data or DNA profile data or dental structure or other biometric feature of an individual. Once the information has been captured, it can be saved locally on the mobile device or remotely on a computer server or in a database. FIG. 8D represents detail similar to that found for an Interpol victim identification 835 whereby the head shape profile may be typed, selected and input by touch screen or by use of a joy stick and click. FIG. 8E represents the automatic collection and entry of GPS coordinate data indicative of a location, for example, of an accident or crime scene or current whereabouts of an individual possessing the mobile telephone. Simultaneously, a clock and calendar may provide date and time for each entry collected of biometric information. If no location manager is found or available, previously acquired GPS coordinate data can be utilized, optionally with an informative message, for example as shown.

Figure 9:
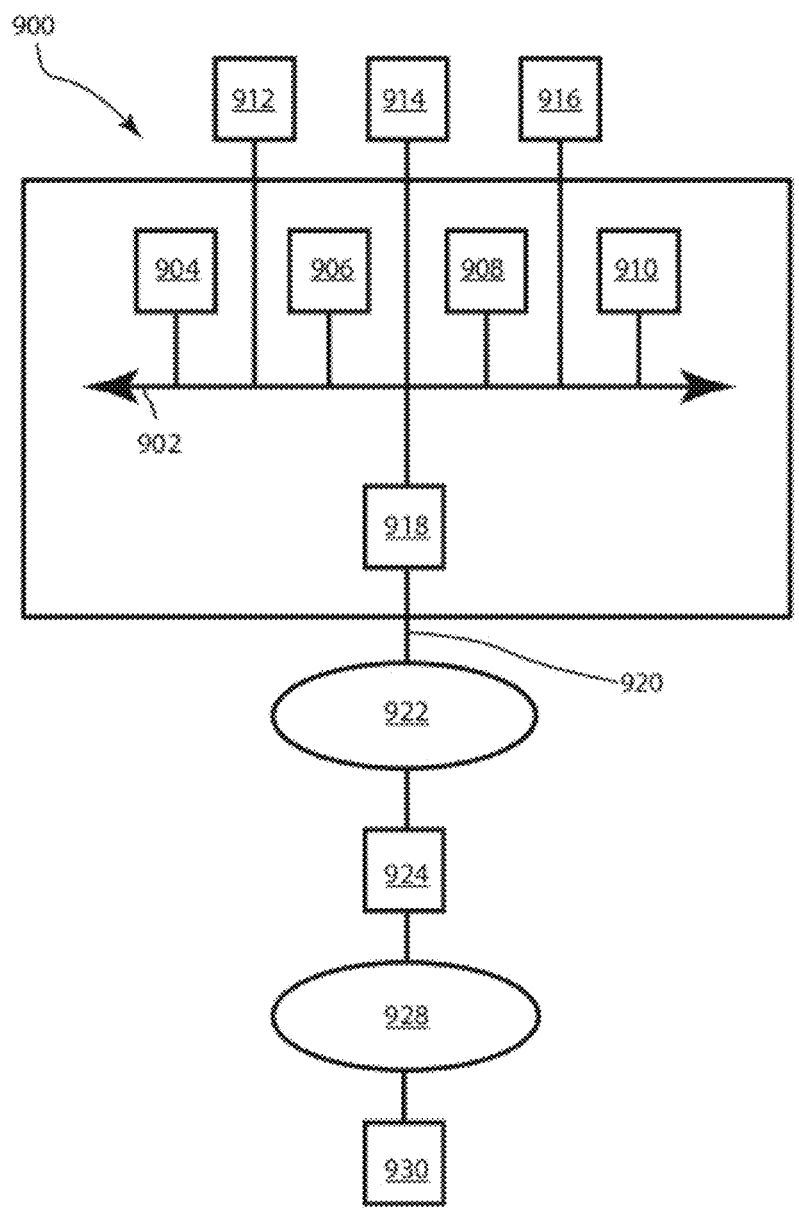

Comparison may be done manually or, according to a computer-implemented algorithm on a computer system according to FIG. 9. Methods of the first embodiment and subsequent embodiments may be utilized in connection with computer readable media which may be provided for temporary or permanent storage in a personal computer, intelligent telecommunications device or other computer or computer system 100 comprising one or more parallel processors known in the art. FIG. 9 is a block schematic diagram that illustrates a computer system 900 upon which at least one embodiment of the invention may be implemented. Computer system 900 includes a bus 902 or other communication mechanism for communicating information, and at least one processor 904 coupled with bus 902 for processing information. Computer system 900 also includes a main memory 906, such as a random access memory ("RAM") or other dynamic storage device, coupled to bus 902 for storing information and instructions to be executed by processor 904. Main memory 906 also may be used for storing temporary variables or other intermediate information during execution of instructions to be executed by processor 904 such as a biometric data collection and identification software application or a disaster victim identification software application. Computer system 900 may further include a read only memory ("ROM") 908 or other static storage device coupled to bus 902 for storing static information and instructions for processor 904. A storage device 910, such as a magnetic disk, optical disk, solid-state memory, or the like, may be provided and coupled to bus 902 for storing biometric information and computer instructions. A storage device may be removable using a coupling mechanism such as a universal serial bus (USB) (see USB port 174, FIG. 1B) or other hardware specific to the type of storage hardware, such as a CompactFlash, SD, or microSD card reader or port. A removable storage device may be utilized to transfer information to or from computer system 900. Any of memories 906, 908, 910 may retain program instructions according to any embodiment of automated data support (ADS) for selecting family data hypothetically related to an individual, for collecting missing person profile data or profile data for a family pedigree or for associating unknown specimens with family pedigrees.

Computer system 900 may optionally be coupled via bus 902 to a display 912, such as a cathode ray tube ("CRT"), liquid crystal display ("LCD"), plasma display, television, small intelligent mobile telephone display 110 or the like, for displaying information to a computer user. Display 912 may provide a virtual keyboard for data input, a real keyboard, a joystick and selector, a fingerprint reader or a one or two dimensional bar code reader via camera 180 or a touch screen. Alternatively, information may be delivered to or collected from a computer user or another computer system or computer program using a communication interface 918 or removable storage device. Communication interface 918 can function as an interface between computer system 900 and additional devices for collection of information, such as a fingerprint reader, a camera, an iris scanner and light source, a DNA analyzer or mass spectrometer, or other devices as are well-known in the field. Communication interface 918 can enable communication using wires, wirelessly (e.g., Bluetooth or WiFi) optical fiber, infrared light-emitting diode and photo reception, carrier wave, or other technologies well-known in the art. There may be more than one communication interface 918. An input device 914, which may include a physical or virtual keyboard including alphanumeric and other keys, may be coupled to bus 902 for communicating information and command selections to processor 904. An optional type of user input device is cursor control 916, such as a mouse, trackball, stylus, or cursor direction keys, for example, as may be found on some personal data assistants (PDA's) for communicating direction information and command selections to processor 904 and for controlling cursor movement on display 912. This input device typically has two degrees of freedom in two axes, a first axis (e.g., x) and a second axis (e.g., y), that allows the device to specify positions in a plane. This input device may be combined with a display device such as a LCD with a touch screen, commonly found on mobile telephones or other telecommunications or presentation devices such as the Apple iPad or a computer tablet using the Android operating system. Alternatively, information and command selections may be communicated to processor 904 using a communication interface 918. Optionally, separate communication interfaces may be used to deliver information to a computer user or another computer system such as a remote server 250 or computer program, and to communicate information and command selections to processor 904.

The invention is related to the use of computer system 900 for automated decision support, for collection of biometric data, specimen data and fingerprint data at a disaster site, crime or accident site or site of a selected family member or a laboratory and for identifying an unknown biological specimen as likely related to a family comprising at least a first and second family member. According to one embodiment of the invention, identifying an unknown biological specimen or individual as likely related to a family comprising at least a first and second family member is provided by computer system 900 in response to processor 904 executing one or more sequences of one or more instructions contained in main memory 906, for example, in accordance with ADS and known missing persons/kinship analysis (MP/KN) developed at the University of Tennessee and disclosed in published U.S. Patent Application Nos. 2008/0040046 of Feb. 14, 2008, (now U.S. Pat. No. 8,271,201 issued Sep. 18, 2012), and 2010/0138374 of Jun. 3, 2010, (now U.S. Pat. No. 8,301,392 issued Oct. 30, 2012). Such instructions may be read into main memory 906 from another computer-readable medium, such as storage device 910. Execution of the sequences of instructions contained in main memory 906 causes processor 904 to perform the process steps described herein. In alternative embodiments. hard-wired circuitry may be used in place of or in combination with software instructions to implement embodiments of the invention. For example, a field-programmable gate array (FPGA) or application-specific integrated circuit (ASIC) may be used. Such a device can, for example, implement associative memory to aid in indexing, search, and retrieval of biometric information stored in a database. A second example is use of a FPGA or ASIC to speed up calculation of a likelihood function used to rank profiles of biometric information. Thus, embodiments of the invention are not limited to any specific combination of hardware circuitry and software. Indexing methods such as those disclosed in U.S. Pat. Nos. 6,741,983, 7,272,612, 7,454,411, 7,769,803, 7,882,106, 8,060,522, and 8,099,733 may be utilized to enable fast retrieval of information similar to information desired in a query of the database.

The term "computer-readable medium" as used herein refers to any medium that participates in providing instructions to processor 904 for execution or storing information in a form that can be accessed by the processor. Such a medium may take many forms, including but not limited to, non-volatile media, volatile media, and transmission media. Non-volatile media includes, for example, optical or magnetic disks, solid state memories, and the like, such as storage device 910. Volatile media includes dynamic memory, such as main memory 906. Transmission media includes coaxial cables, copper wire and fiber optics, including the wires that comprise bus 902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, solid-state memory, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read. Various forms of computer readable media may be involved in carrying one or more sequences of one or more instructions to processor 904 for execution.

Computer system 900 may include one or more communication interfaces 918 coupled to bus 902. Communication interface 918 provides a two-way data communication coupling 205, 215 to a network link 920 that is connected to a local network 922. For example, communication interface 918 may be an integrated services digital network ("ISDN") or digital subscriber line ("DSL") card or a modem to provide a data communication connection to a corresponding type of telephone line or wireless link. Preferably, communications transmitted over such a link 205, 215 are encrypted or otherwise protected according to known encryption schemes and/or watermarking algorithms to uniquely identify a source, for example, of a fingerprint capture device or camera or other input source. As another example, communication interface 918 may be a network card (e.g., an Ethernet card) to provide a data communication connection to a compatible local area network ("LAN") or wide area network ("WAN"), such as the Internet or a private network. Wireless links are implemented in the about-to-be-described example of running a mobile disaster victim identification algorithm on an intelligent telecommunications device using, for example, Bluetooth, or third generation ("3G") or fourth generation ("4G") wireless technologies such as WiMax or LTE. In any such implementation, communication interface 918 sends and receives electrical, electromagnetic or optical signals that carry digital data streams representing various types of information. For example, a forensic investigation may require a data communication connection to a biometric information database comprising for example, fingerprint data, DNA profile data, cornea/iris data or other biometric forensic information. A second example is use of one or more data communication connection(s) to access at least one database at remote server 250 used to store DNA and/or non-DNA information. Portions of the computations associated with the collection and identification of biometric data as described herein may be distributed across multiple computer systems 900 which may communicate using one or more communication interfaces 918.

Network link 920 typically provides data communication through one or more networks to other data devices. For example, network link 920 may provide a connection through local network 922 to a host computer 924 or to data equipment operated by an Internet Service Provider or private network service provider ("ISP"). It is intended that such a service provider may operate in a "cloud" computing environment such that it is a web accessible service for, for example, identifying a perpetrator of a crime or terrorist act, a victim or missing person. An ISP in turn provides data communication services through a packet data communication network such as the worldwide network commonly referred to as the "Internet" 928, an extranet, an intranet or other private or public network. An example of a private network is a secure data network linking law enforcement agencies and used for transmission of DNA and/or non-DNA information. Local network 922 and Internet 928 both use electrical, electromagnetic or optical signals that carry digital data streams. The signals through the various networks and the signals on network link 920 and through communication interface 918, which carry the digital data to and from computer system 900, are exemplary forms of carrier waves transporting the information.

Computer system 900 can send messages, commands and data and receive messages, commands and data, including program code, through the network(s), network link 920 and communication interface 918. In the Internet example, a server 930 (e.g. remote server 250) might transmit a requested code for an application program (ADS or other applications such as LSD or STRESP or peak fitting) through Internet 928, host computer 924, local network 922 and communication interface 918. In accordance with the invention, one such downloaded application provides a method of identifying an unknown biological specimen as likely related to a family comprising at least a first and second family member or a biometric information collection and identification software application or a mobile disaster victim identification application or a least squares deconvolution mixture application for resolving DNA mixtures or a peak-fitting algorithm or an automated expert system.

The received code may be executed by processor 904 as it is received, and/or stored in storage device 910, or other tangible computer-readable medium (e.g., non-volatile storage) for later execution. In this manner, computer system 900 may obtain application code and/or data in the form of an intangible computer-readable medium such as a carrier wave, modulated data signal, or other propagated signal.

Computer system 900 can be configured using the methods of this invention to provide services across a network to forensic personnel having client computers or intelligent telecommunications devices capable of connection to a network or other communication interface. Such services can include assistance in identification of unidentified remains or portions of remains and storage of DNA and non-DNA information about known individuals and missing persons and their relationships, or a family pedigree. These services can also be provided to other software, located in either computer system 900 or a separate computer system such as remote server 250 or a cloud service connected by a network, network link, or communication interface to computer system 900. The services can be protected using methods of authentication and/or encryption and/or watermarking that are known in the fields of computer science and computer security in order to ensure data are neither compromised nor disclosed and to trace all accesses to the data. The computer system 900 and other associated information storage and communication components can be protected using devices and methods that are known in the fields of computer science and computer security, such as with firewalls, physical access controls, power conditioning equipment, and backup or redundant power sources. The protection devices and methods, embodied as hardware, software or a combination of hardware and software, may be incorporated in computer system 900 or exist as separate components typically connected by a network or other communications hardware. The information stored by computer system 900 and computer-readable media can be further protected using backup or redundant information storage systems, such as those that are well-known in the art. Examples include tape storage systems and RAID storage arrays.

Figure 10A:
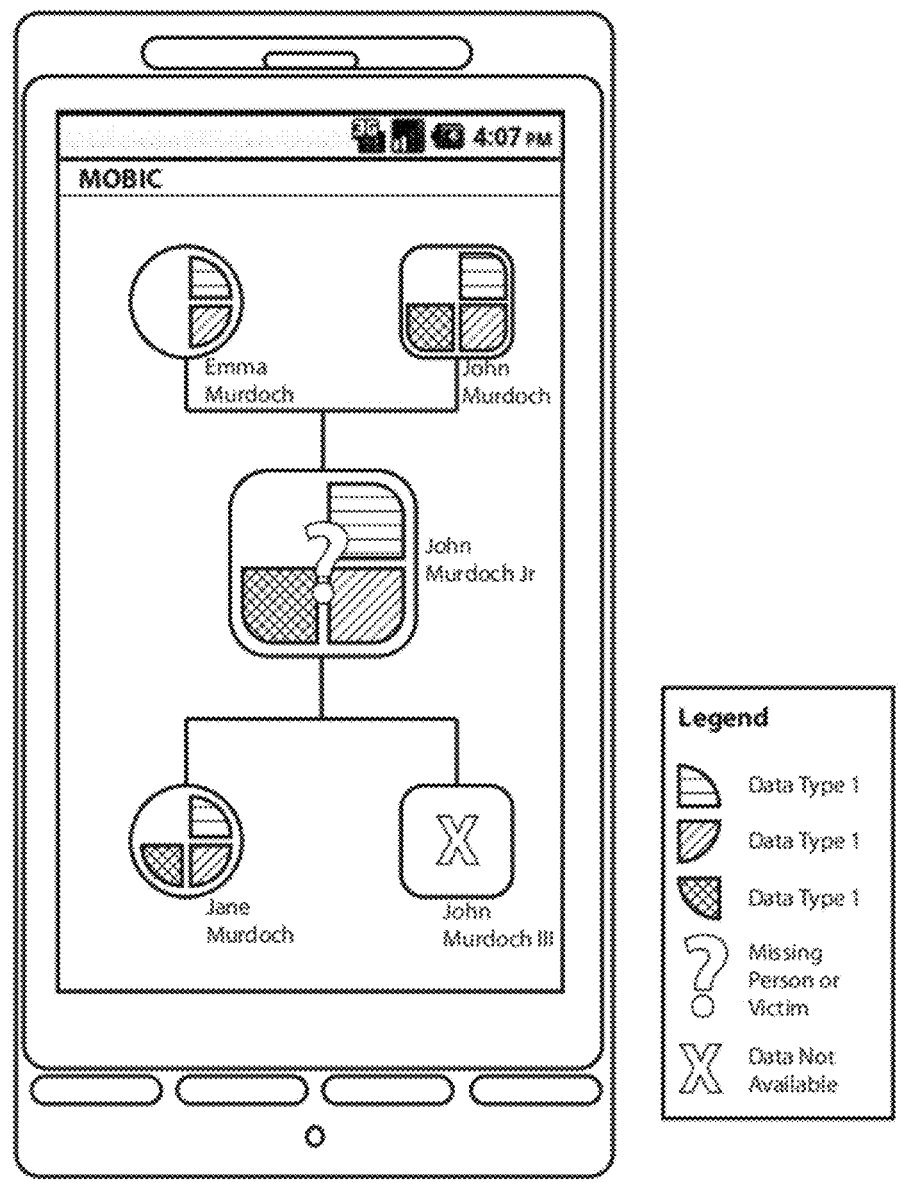
FIG. 10A provides a completed exemplary pedigree chart for mother, Emma, father, John, missing person John, Jr., son, John, III and daughter, Jane whereby collected profile data may be indicated by graphics or icons with shading or color to indicate the type of collected profile data, which may be DNA profile data, any other type of biometric data such as the sex, weight, height, age, or birthday of the individual, or one or more fingerprints, an iris image, skin, hair, or eye color, or any other measurement that describes a measurable attribute of a person, animal, body, body part, or remain. A graphic or icon such as a question mark (shown) may be used to indicate a questioned sample or missing person, or that a sample of known or unknown origin may be compared against the biometric or other data available for the individual indicated by the graphic in the pedigree. A second graphic such as an 'X' (shown) may be used to indicate that information, or some subset of information, is missing or not available for the individual indicated by the second graphic.
Figure 10B:
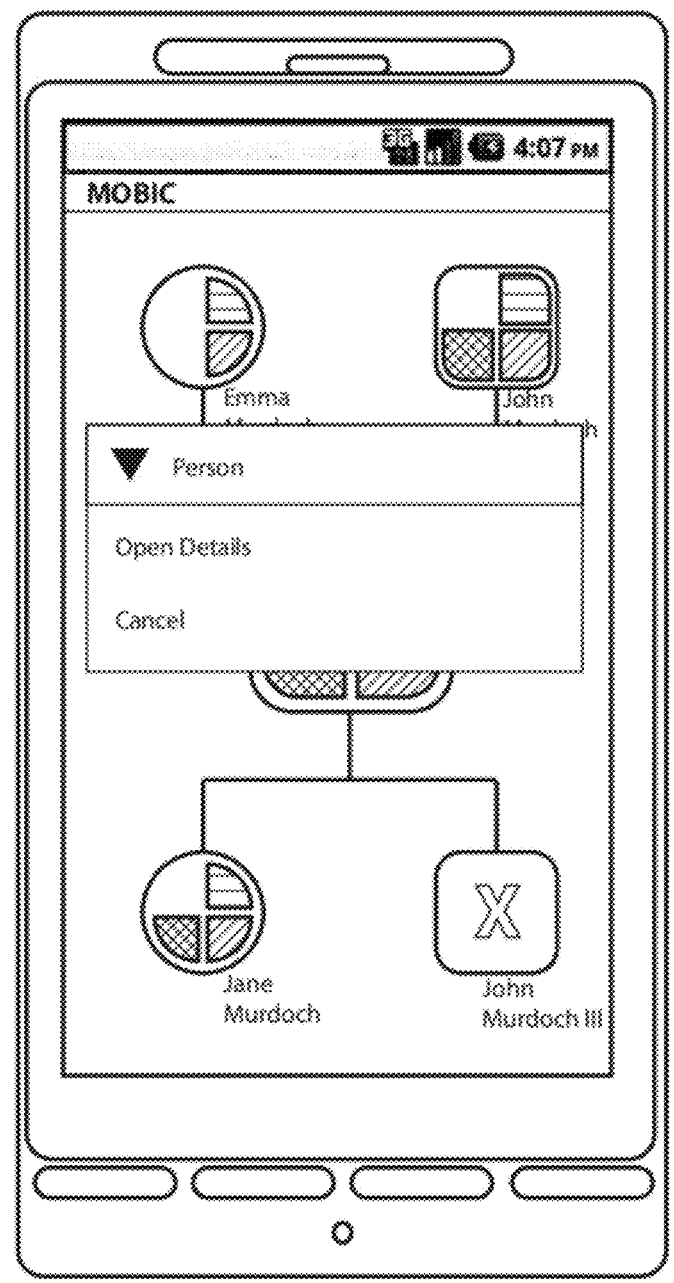
FIG. 10B shows that one may open details for a selected person; and where a pedigree chart may be automatically generated using any combination of entered or stored data such as a family relationship or one or more DNA profiles.
Figure 10C:
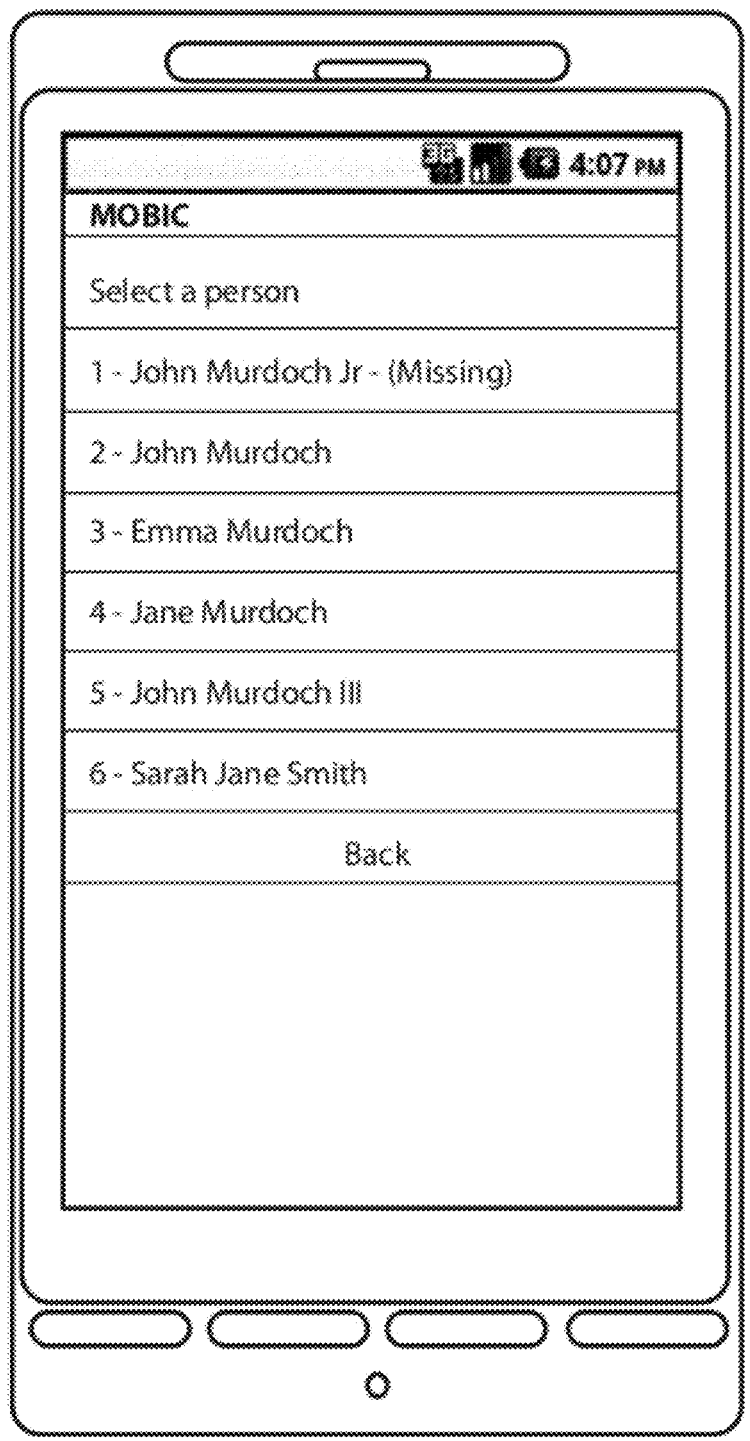
FIG. 10C provides a corresponding Select a Person screen related to FIG. 10B for selecting one of the family members of the pedigree of FIG. 10A including a further person Sarah Jane Smith, not shown in the pedigree chart of FIG. 10A.
Figure 11A:
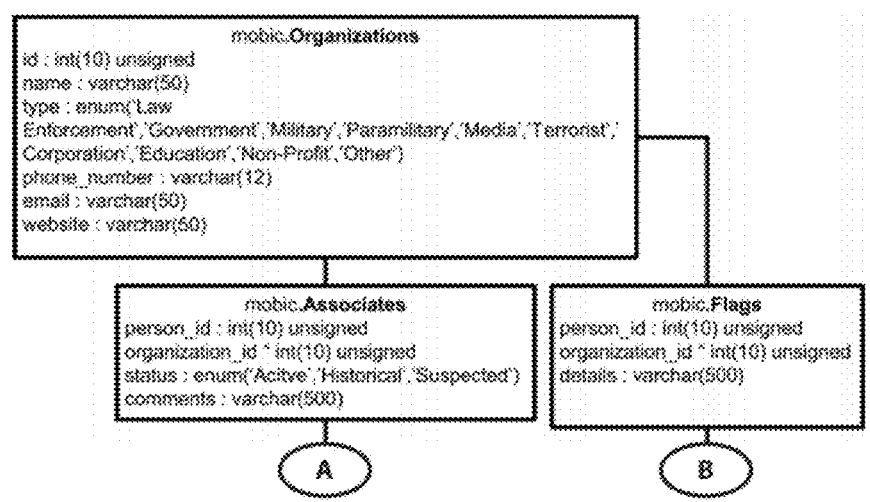
FIGS. 11A, 11B, 11C, and 11D provide an example of a database schema for the database of remote server 250 of FIG. 2.
Figure 11B:
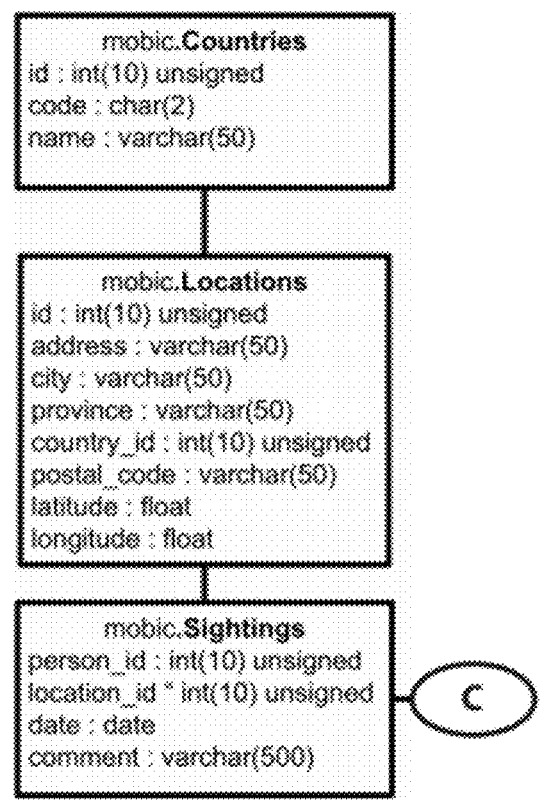
Figure 11C:
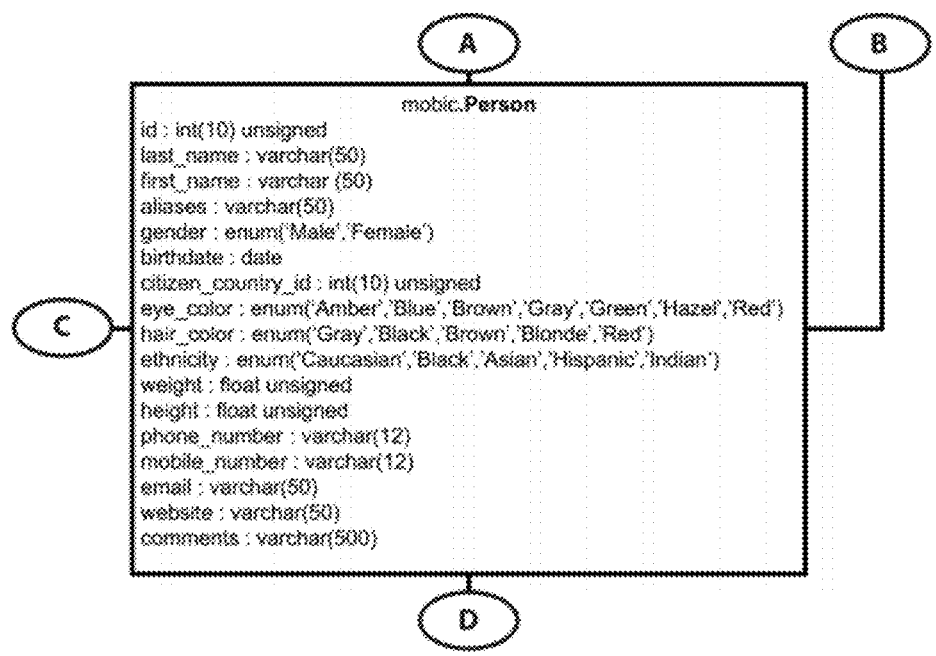
Figure 11D:
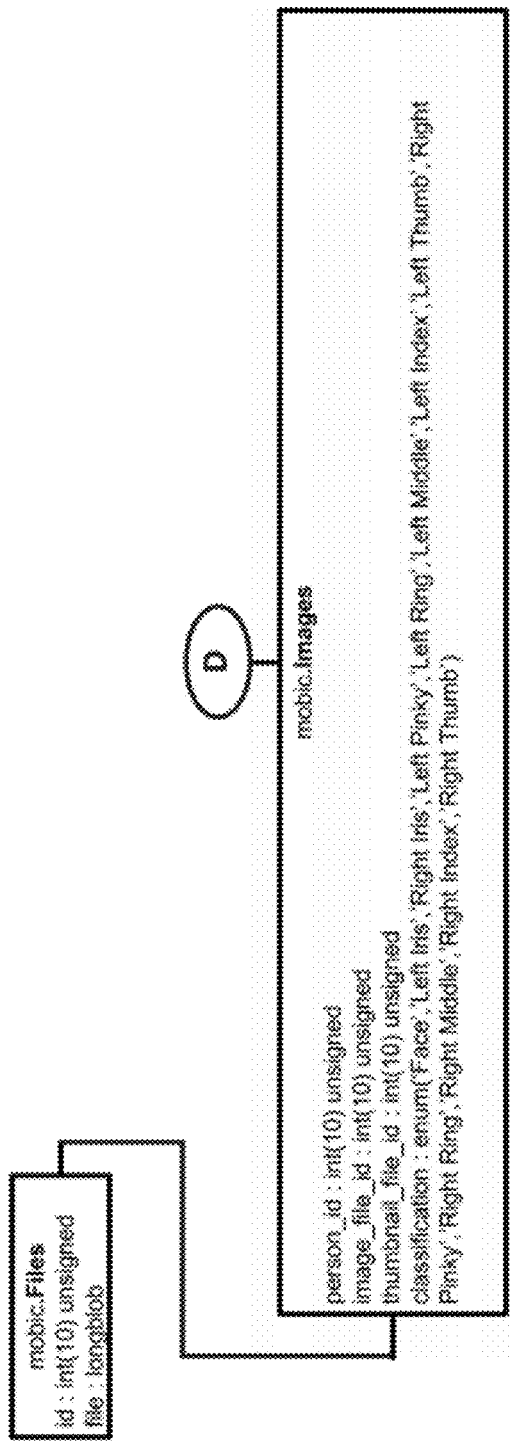

FIG. 10A provides a completed pedigree chart for mother, Emma, father, John, missing person John, Jr., son, John, III and daughter, Jane whereby collected profile data may be indicated by color. John, III has not been entered. Neither John III or Jane are required to obtain a match given the presence of both profiles for mother, Emma and father, John as discussed in the discussion of automatic decision support (ADS). FIG. 10C provides a corresponding Select a Person screen for an open details screen of FIG. 10B whereby one may select one of the family members of the pedigree of FIG. 10A including a further person Sarah Jane Smith, not shown in the pedigree chart of FIG. 10A. As discussed above, Sarah may be the victim of a rape and her DNA profile may be known. John Murdoch Jr. may be a hypothetical perpetrator who is missing and has no profile data on file but may be identified using least square deconvolution and the pedigree including father, mother and daughter.

After a pedigree and associated typed family members are entered or defined, an unknown sample that has been that has been typed and entered or defined may be evaluated against the pedigree by a missing persons/kinship (MP/KN) software application as described in U.S. Published Application No. 2008/0040046, published Feb. 14, 2008, (now U.S. Pat. No. 8,271,201 issued Sep. 18, 2012). A pedigree may be directly entered, retrieved from a database, or constructed from known relationships among family members. The relationship data may be entered or acquired using the mobile device 100, or the data may be retrieved by the mobile device from a local or remote database. Portions of the relationship or pedigree data may be obtained from different sources and at different times. A least squares deconvolution algorithm may be used if a mixture of DNA from two individuals is present in a sample, and/or a peak fitting algorithm, a mass spectrometry algorithm, or an expert system may be applied to perform analysis of data and transform it into a more useful form such as the DNA profiles of two likely contributors to a mixture or an accurate DNA profile. Other algorithms may come to mind to one of ordinary skill in the art for identifying a hypothetical missing person, crime victim, crime perpetrator or contributor to a DNA mixture. Such algorithms may utilize other data instead of or in addition to DNA profile data, such as SMT, facial profile, biometric data such as iris scans or blood vessel patterns in the skin, or fingerprints. Either the hypothetical pedigree is proven feasible or it is not feasible, or an unknown sample can be ranked against the pedigree, and that result may be returned by the MP/KN algorithm for display to the user.

FIGS. 11A, 11B, 11C, and 11D show a schema of an exemplary database running on a server 250 to which the biometric data mobile device 100 communicates. Preferably, for the purposes of added security, deployment and management, a service layer is implemented in software that accepts a communications connection and data requests and optionally other commands from a mobile biometrics device 100, communicates with a database implemented in one of many possible well-known database products such as MySQL, Oracle, and DB2 to store or obtain information on behalf of the client 100, and transmits information back to the client 100 as a result of the exchange with the database to satisfy the client's request. The connection between the client 100 and the software service layer may be persistent or may be restarted with each request, and it can be implemented using either a wired or wireless network such as Ethernet, including Fast Ethernet and Gigabit Ethernet, 3G or 4G wireless, or WiFi. Communication between the client 100 and the database can be implemented using a web service interface, preferably using JBOSS middleware or another Java EE based Application Server. Enterprise Beans can then be used to perform transactions on the database. Another approach is to implement services offered by a web server using the PHP, Perl, or Python programming language. An alternative, and well-known approach, is to use a direct connection between the client and one or more databases using a database vendor's application programming interface or other similar tools such as an ODBC layer. Some database vendors, such as Oracle, have adopted database client, service, or software as a service approaches using standardized languages or software platforms such as Java. Other languages such as Java, C, C++, or C# can be used in each of these scenarios.

The schema is shown in FIGS. 11A, 11B, 11C, and 11D, by example, as a collection of database tables and may be contained in a single database or multiple databases. The database scheme is preferably relational, as is shown in the figure, but other methods may be utilized. For example, the methods disclosed in U.S. Pat. Nos. 6,741,983, 7,272,612, 7,454,411, and 7,769,803 may be used. The service layer may also be utilized to communicate with computational services such as one that implements a method for DNA mixture deconvolution, as disclosed in U.S. Pat. Nos. 7,162,372 and 7,672,789. or such as one that implements a method for determining a likelihood ratio such as is disclosed in U.S. patent application Ser. No. 11/467,834, U.S. Published Patent Application No. 2008/0040046, (now U.S. Pat. No. 8,271,201 issued Sep. 18, 2012). or such as one that implements a method to support decision making in associating an unknown biological specimen with a family such as is disclosed in U.S. patent application Ser. No. 12/684,539, U.S. Published Application No. 2010/0138374, (now U.S. Pat. No. 8,301,392 issued Oct. 30, 2012).

All patents, patent applications, articles and other references cited in this disclosure and identified above are expressly incorporated herein by reference as to their entire contents. Further, while several preferred embodiments and methods have been described using specific terms and a specific example of an intelligent wireless telephone, such description is for illustrative purposes only, and it is to be understood that changes and variations may be made without departing from the spirit or scope of the following claims.

What we claim is:

1. A biometric mobile communications device comprising
a camera adapted to capture individual biometric data of one of an iris, cornea and face image, a fingerprint image, and a bar code image for storage in memory of the device;
a DNA profile data input connection for receiving DNA profile data collected for an individual as individual biometric data by one of DNA specimen analysis, DNA mixture deconvolution analysis and mass spectrometry data analysis for storage as individual biometric data in memory of the device;
a touchscreen display for receiving input data of a selection of individual biometric data for storage, for displaying capture of the one of the iris, cornea and face image, a fingerprint image, and a bar code image and for displaying a family pedigree of at least one missing person responsive to the individual biometric data and displaying one further member of the family pedigree;
a communications interface for communicating the individual biometric data to a remote database server, the communications interface comprising one of a wired and a wireless link to the remote database server;
a global positioning system for determining a location of collection of the individual biometric data for storage in the device memory with the individual biometric data;
a real time clock for associating a current date and time of day to the collection of the individual biometric data;
the device memory for storing the selection of individual biometric data, camera image output, DNA profile data received via the data input connection, data received via the communications interface and the time and the location of collection of the individual biometric data; and
a data processor, responsive to the device memory, for communicating the individual biometric data comprising the touchscreen display input, one of a fingerprint, an iris image and a bar code image, time and location data of collection of the individual biometric data and the individual biometric data including DNA profile or mass spectrometry data to a remote server for retrieving an identification of an individual and a likelihood of the identification of the individual for display on the display.

2. The biometric mobile communications device of claim 1, the display further comprising a sequence of menu screens including a main menu screen and subordinate screens for browse and search features whereby a plurality of profiles of different individuals associated with the individual in rank order in accordance with the likelihood of the identification of the individual are retrieved and displayed on the display.

3. The biometric mobile communications device of claim 1 further comprising a radio frequency identification tag reader wherein the individual comprises one of a human being and an animal, the tag reader adapted to read a radio frequency identification tag of the one of the human being and the animal.

4. The biometric mobile communications device of claim 3 further comprising a radio frequency identification tag reader receiver for receiving the unique identification of one of an animal and an individual human being for storage in the device memory.

5. The biometric mobile communications device of claim 1, the communications interface further comprising a microphone for receiving a sound input, the data processor programmed for storage in the device memory as individual biometric data, one of the data processor and the remote database server for matching the sound input to an identity of an individual.

6. The biometric mobile communication device of claim 1 further comprising the data input connection for receiving a data analysis output of a portable laboratory for storage in memory of the device, the portable laboratory for analyzing one of breath, a DNA specimen, a mixture of DNA specimens and a body fluid of an individual, the real time clock for associating a current date and time of day to the data analysis output and the geographical positioning system for associating a geographical location with the data analysis output.

7. The biometric mobile communication device of claim 5, the microphone adapted to provide a sound input from an identified individual to the data processor, the data processor having sound to text conversion special purpose computer software for outputting text data to the communications interface, the communications interface for transmitting the output text data and a location of collection of the biometric data to the remote database server.

8. The biometric mobile communication device of claim 1, the DNA profile collection comprising DNA specimen analysis, the DNA specimen analysis using a lab-on-a-chip DNA profile device.

9. The biometric mobile communication device of claim 1, the displayed further member of the family pedigree having a known DNA profile, the known DNA profile for comparison with that of the missing person to identify the missing person and a likelihood that the missing person is the individual via one of the data processor and a processor of the remote database server.

10. The biometric mobile communication device of claim 1 further comprising one of an infrared and ultraviolet light for illuminating an event scene for the camera, the camera for further capturing an event scene for storage in device memory with the location of collection of biometric data determined by the global positioning system.

11. A biometric mobile communications device comprising
a memory of the device for storing individual biometric data;
a camera adapted to capture individual biometric data comprising one of an iris, a cornea and a face image, a fingerprint image, an event scene image and a bar code image for storage in the memory of the device;
a global positioning system for determining a location of collection of the individual biometric data for storage in the device memory;
a day and time clock for capturing individual biometric data collection time and date data for storage in the device memory;
a connection for receiving a data analysis output of a portable laboratory for storage in memory of the device, the portable laboratory for analyzing one of breath and a body fluid of an individual, a DNA specimen, a mixture of DNA specimens, and a mass spectrometry analysis of a specimen, the data analysis output comprising individual biometric data for identifying an individual;
a communications interface for communicating with a remote database server;
a touchscreen display for receiving input data of a selection of individual biometric data for storage, for displaying capture of the one of the iris, cornea and face image, a fingerprint image, and a bar code image and for displaying a family pedigree of at least one missing person responsive to the stored individual biometric data and of one further member of the family pedigree; and a data processor, responsive to the device memory, for communicating individual biometric data comprising one of a fingerprint, an iris image and a bar code image and other individual biometric data to a remote server for retrieving an identification of an individual and a likelihood of the identification of the missing person as the individual for display on the display.

12. The biometric mobile communication device of claim 11, the communications interface further comprising a microphone for receiving a sound input for storage in the device memory, the remote server for matching the sound input to an identity of an individual.

13. The biometric mobile communication device of claim 11 further comprising a radio frequency identification tag reader receiver for receiving the unique identification of an animal individual for storage in the device memory or the unique identification of a shipment of a package.

14. The biometric mobile communication device of claim 11, the display for displaying possible matches of biometric data to individuals in rank order according to likelihood ratio of a match to a known individual.

15. A biometric mobile communication device comprising:
   a memory of the device for storing individual biometric data;
   a camera adapted to capture individual biometric data comprising one of an event scene image and a bar code image for storage in the memory of the device;
   a global positioning system for determining a location of collection of the individual biometric data for storage in the device memory;
   a day and time clock for capturing individual biometric data collection time and date data for storage in the device memory;
   a connection for receiving a data analysis output of a portable laboratory for storage in memory of the device, the portable laboratory for analyzing one of human tissue, breath and a body fluid sample of an individual, a DNA specimen, a mixture of DNA specimens, and a mass spectrometry analysis of a specimen, the data analysis output comprising individual biometric data for identifying an individual;
   a communications interface for communicating with a remote database server;
   a touchscreen display for receiving input data of a selection of individual biometric data for storage, for displaying capture of the one of the iris, cornea and face image, a fingerprint image, and a bar code image and for displaying a family pedigree of at least one missing person responsive to the stored individual biometric data and of one further member of the family pedigree; and
   a data processor, responsive to the device memory, for communicating individual biometric data comprising individual biometric data to a remote server for retrieving an identification of an individual as at least two candidate missing persons and a likelihood ratio of the identification and ranking by likelihood ratio of the two candidate missing persons as the individual for display on the display.

16. The biometric mobile communication device of claim 15, the event scene further comprising a skin portion of an individual as biometric data of a vascular structure within the skin or details of an eye portion.

17. The biometric mobile communication device of claim 11, the camera for capturing a series of images of an event scene over time, the data processor for determining changes in the event scene over time.

18. The biometric mobile communication device of claim 11, the communications interface further comprising an interface to a geographic information system for generating a map of an event scene area for storage in memory with event scene images.

19. The biometric mobile communication device of claim 1 further comprising a data input device and data input screens of the display for entering biometric data for an individual comprising four of height, weight, age, sex and ethnic origin.

20. The biometric mobile communication device of claim 1 further comprising a means for measuring temperature, humidity, air pressure at an event scene for storage in the device memory with the biometric data.

* * * * *